(12) United States Patent
Makansi

(10) Patent No.: US 11,998,753 B2
(45) Date of Patent: *Jun. 4, 2024

(54) WIRELESS NEURAL STIMULATOR WITH INJECTABLE

(71) Applicant: StimAire, Inc., Tucson, AZ (US)

(72) Inventor: Tarek Makansi, Tucson, AZ (US)

(73) Assignee: StimAire, Inc., Tucson, AZ (US)

( * ) Notice: Subject to any disclaimer, the term of this patent is extended or adjusted under 35 U.S.C. 154(b) by 588 days.

This patent is subject to a terminal disclaimer.

(21) Appl. No.: 16/991,593

(22) Filed: Aug. 12, 2020

(65) Prior Publication Data

US 2021/0023381 A1 Jan. 28, 2021

Related U.S. Application Data

(63) Continuation of application No. 16/716,364, filed on Dec. 16, 2019, now Pat. No. 10,744,339, which is a
(Continued)

(51) Int. Cl.
*A61N 2/02* (2006.01)
*A61N 1/40* (2006.01)
*A61N 2/00* (2006.01)

(52) U.S. Cl.
CPC ............... *A61N 2/02* (2013.01); *A61N 1/40* (2013.01); *A61N 2/006* (2013.01); *A61N 2/008* (2013.01)

(58) Field of Classification Search
CPC ............. A61N 2/00–02; A61N 1/372; A61N 1/37205; A61N 1/37223; A61N 1/37229; A61N 1/37276; A61N 1/3787; A61N 1/40–406; G06K 7/086; G06K 7/10336; H02J 50/12
See application file for complete search history.

(56) References Cited

U.S. PATENT DOCUMENTS

| 5,193,540 A | 3/1993 | Schulman et al. |
| 5,195,941 A * | 3/1993 | Erickson .................. A61N 2/02 |
| | | 600/15 |

(Continued)

FOREIGN PATENT DOCUMENTS

| EP | 2130566 A1 | 12/2009 |
| JP | 2006520672 A | 9/2006 |

(Continued)

OTHER PUBLICATIONS

English translation of Office Action for JP Application No. 2019-541687, dated Aug. 27, 2021.
(Continued)

*Primary Examiner* — Christine H Matthews
*Assistant Examiner* — Marc D. Honrath
(74) *Attorney, Agent, or Firm* — Dorsey & Whitney LLP

(57) ABSTRACT

Neural stimulator systems with an external magnetic coil to produce changing magnetic fields is applied outside the body, in conjunction with one or more tiny injectable objects that concentrates the induced electric field to a highly-targeted location. These systems include a driver circuit for the magnetic coil that allows for high voltage and fast pulses in the coil, while requiring low-voltage power supply that may be powered by a wearable or portable external device, along with the coil and driver circuit.

13 Claims, 34 Drawing Sheets

Related U.S. Application Data continuation of application No. 16/342,508, filed as application No. PCT/US2017/056795 on Oct. 16, 2017, now abandoned.

(60) Provisional application No. 62/561,821, filed on Sep. 22, 2017, provisional application No. 62/454,842, filed on Feb. 5, 2017, provisional application No. 62/408,793, filed on Oct. 16, 2016.

(56) References Cited

U.S. PATENT DOCUMENTS

| | | | |
|---|---|---|---|
| 5,743,844 A | 4/1998 | Tepper et al. | |
| 5,951,459 A * | 9/1999 | Blackwell | A61N 2/02 600/15 |
| 6,179,770 B1 | 1/2001 | Mould | |
| 6,527,695 B1 | 3/2003 | Davey et al. | |
| 6,735,474 B1 | 5/2004 | Loeb et al. | |
| 8,545,378 B2 | 10/2013 | Peterchev | |
| 8,571,654 B2 | 10/2013 | Libbus et al. | |
| 8,666,504 B2 | 3/2014 | Dronov et al. | |
| 9,072,891 B1 | 7/2015 | Rao | |
| 10,744,339 B2 * | 8/2020 | Makansi | A61N 2/02 |
| 2003/0032852 A1 * | 2/2003 | Perreault | A61N 2/006 600/13 |
| 2003/0040291 A1 * | 2/2003 | Brewer | A61N 1/37223 455/127.1 |
| 2005/0131496 A1 * | 6/2005 | Parramon | A61N 1/37205 607/61 |
| 2006/0085041 A1 | 4/2006 | Hastings et al. | |
| 2007/0293916 A1 | 12/2007 | Peterchev | |
| 2008/0306326 A1 | 12/2008 | Epstein | |
| 2009/0018384 A1 | 1/2009 | Boyden et al. | |
| 2009/0018618 A1 * | 1/2009 | Parramon | A61N 1/37252 607/60 |
| 2009/0118779 A1 | 5/2009 | Najafi et al. | |
| 2010/0160712 A1 | 6/2010 | Burnett et al. | |
| 2011/0092780 A1 * | 4/2011 | Zhang | A61B 5/053 600/301 |
| 2012/0019316 A1 * | 1/2012 | Hattersley | H05B 6/06 327/581 |
| 2012/0108883 A1 | 5/2012 | Peterchev | |
| 2012/0302821 A1 | 11/2012 | Burnett | |
| 2013/0066392 A1 | 3/2013 | Simon et al. | |
| 2014/0357933 A1 | 12/2014 | Lee et al. | |
| 2015/0080637 A1 | 3/2015 | Bonmassar et al. | |
| 2015/0148878 A1 | 5/2015 | Yoo et al. | |
| 2016/0175600 A1 | 6/2016 | Amir et al. | |
| 2020/0054889 A1 | 2/2020 | Makansi | |
| 2020/0139149 A1 | 5/2020 | Makansi | |
| 2021/0019316 A1 | 1/2021 | Pang | |

FOREIGN PATENT DOCUMENTS

| | | |
|---|---|---|
| JP | 2007158151 A | 6/2007 |
| JP | 2015213841 A | 12/2015 |
| JP | 6377466 B2 | 8/2018 |
| JP | 6509249 B2 | 4/2019 |

OTHER PUBLICATIONS

Extended European Search Report for Application No. 17860914.5, dated Apr. 20, 2020.
International Search Report and Written Opinion received in PCT/US2017/056795 dated Mar. 8, 2018.
Office Action issued in Canadian Patent Application No. 3,040,164, mailed on Jan. 10, 2024, 3 pages.

* cited by examiner

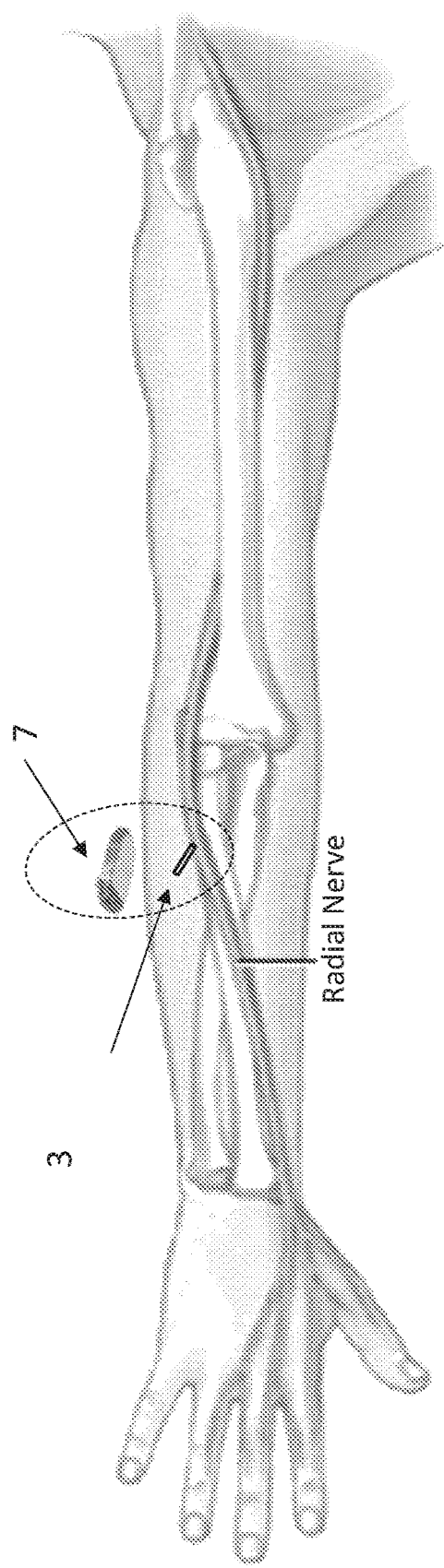
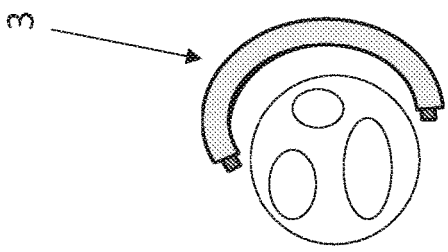
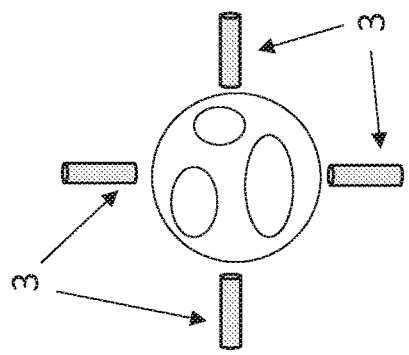
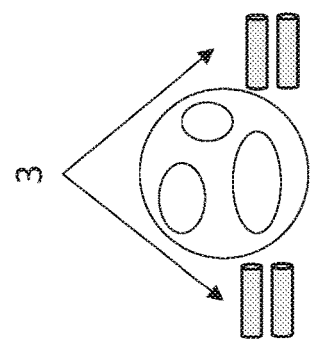
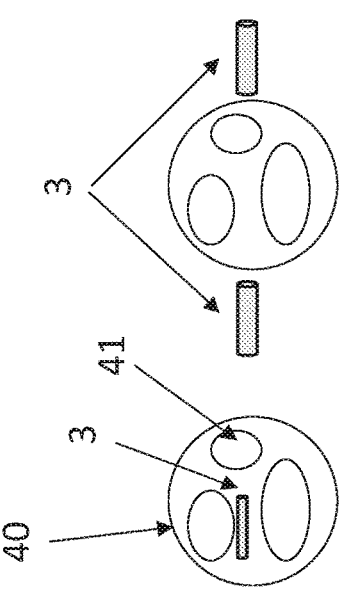
FIG. 4a  FIG. 4b  FIG. 4c  FIG. 4d  FIG. 4e  FIG. 4f

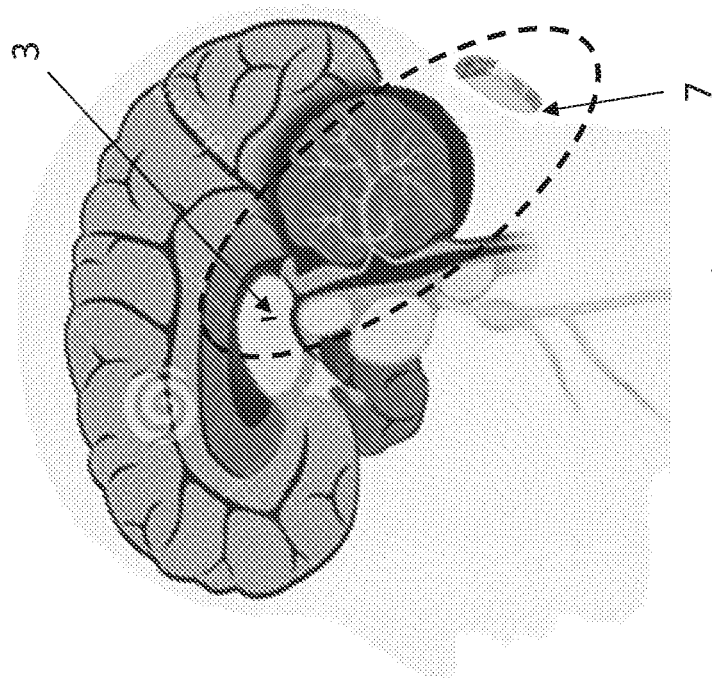
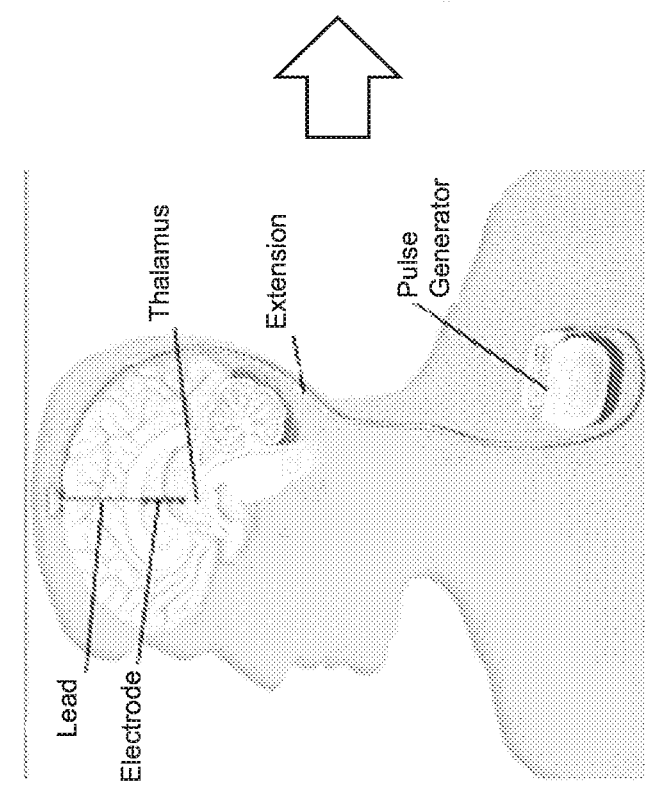
FIG. 6b
FIG. 6a

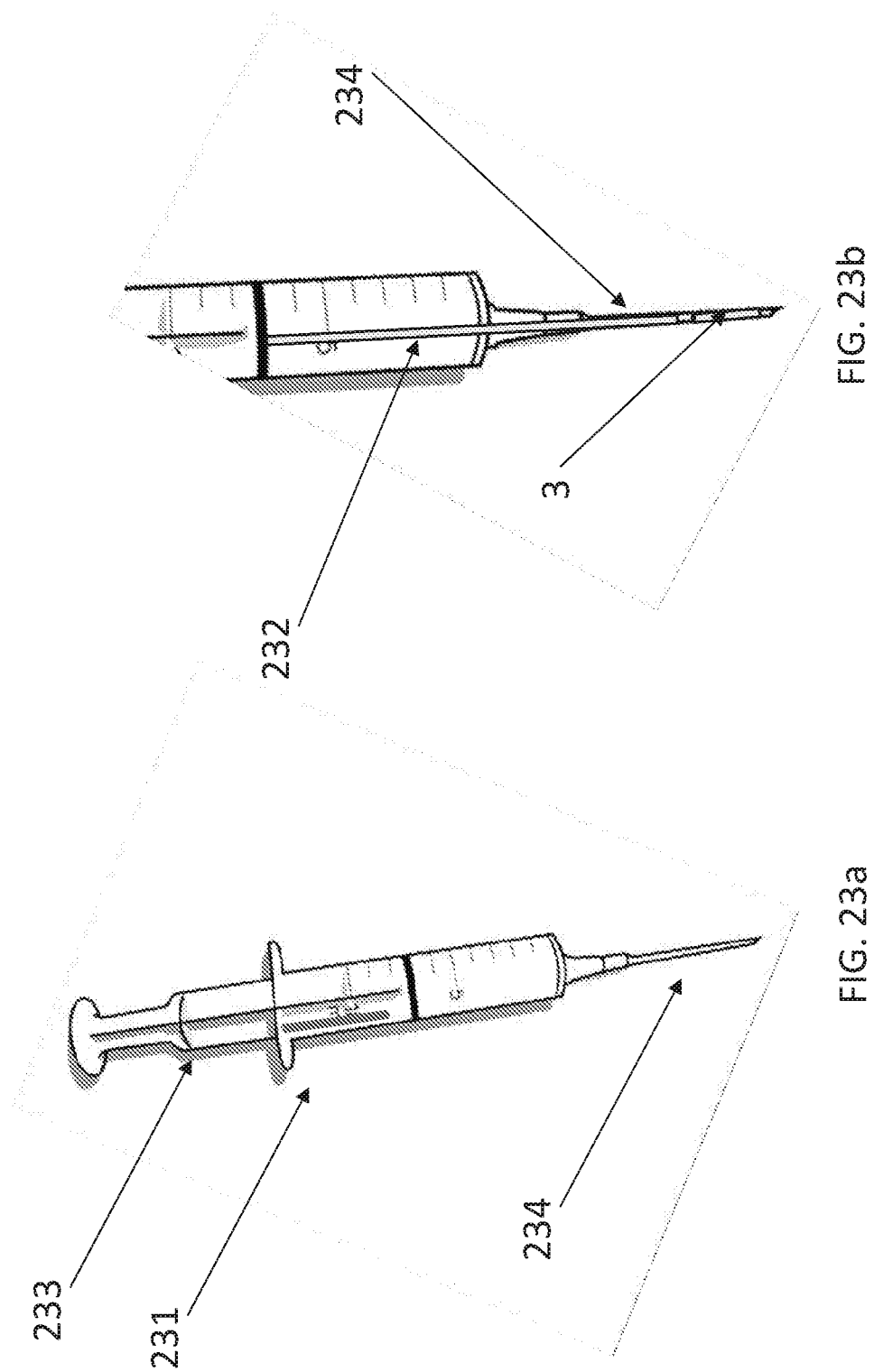

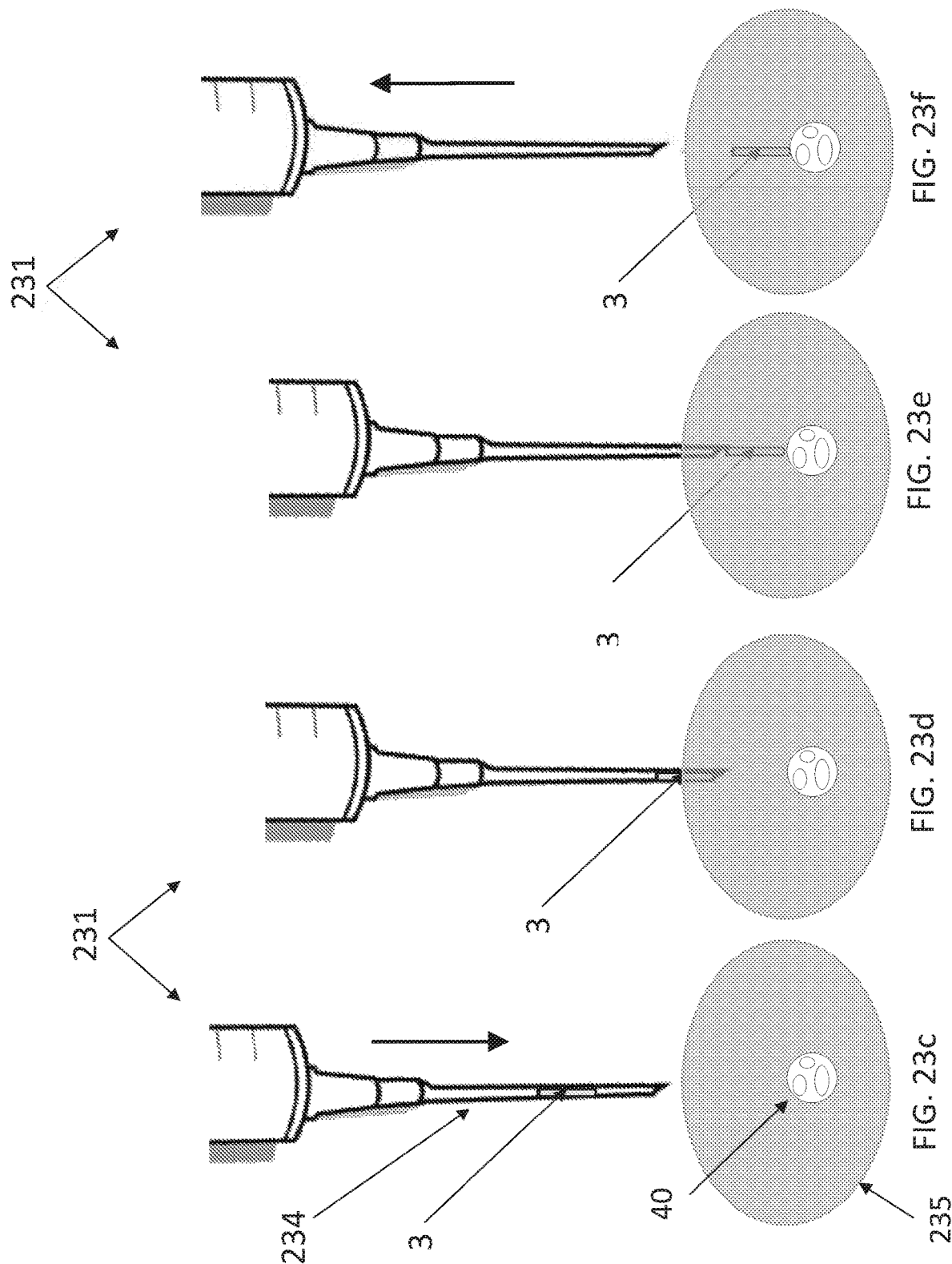

Power Saving Mode Operation

Pulse Shape Flexibility Mode Operation

WIRELESS NEURAL STIMULATOR WITH INJECTABLE

CROSS-REFERENCE TO RELATED APPLICATIONS

This application is a continuation of U.S. application Ser. No. 16/716,367 filed Dec. 16, 2019, now U.S. Pat. No. 10,744,339, which is a continuation of U.S. application Ser. No. 16/342,508, filed Apr. 16, 2019, now abandoned, which is a U.S. National Stage application of PCT Application No. PCT/US17/56795, filed Oct. 16, 2017, which claims the benefit of priority to U.S. Provisional Patent Application Ser. No. 62/408,793, filed on Oct. 16, 2016, U.S. Provisional Patent Application Ser. No. 62/454,842, filed on Feb. 5, 2017, and U.S. Provisional Patent Application Ser. No. 62/561,821, filed on Sep. 22, 2017, each of which is hereby incorporated by reference in its entirety.

BACKGROUND

The human and mammal bodies use electrical signals to achieve sensory input, muscle movements, thoughts, and memory. Over time, these signals are also responsible for neural plasticity, which includes general wiring, rewiring, and de-wiring of the brain. The electrical signals are represented in the mind and body as potentials (voltages) created by ions, not electrons. However, these ion-transported signals can be initiated, negated, or altered by electric fields that originate from outside the body. By Faraday's law of electromagnetics, these electric fields can be generated from changing magnetic fields, hence, the name "magnetic stimulation". Because these signals are initiated from outside the body, magnetic stimulation can be a non-invasive means for altering or improving of almost all bodily and mental functions.

The signals inside the body are "action potentials" that are pulse-frequency modulated, meaning that the pulse rate is related to the intensity of the sensed input, muscular energy, or neuronal message. The shapes of individual pulses are largely the same throughout, having a pulse width of about 1 millisecond and some undershoot after the main pulse. The pulse height is approximately 70 millivolts for sensory signals and somewhat larger for muscle activation. Pulses for the heart, digestive system, and may other organs have other unique characteristics. For the most part, the signals all look the similar when viewed on an oscilloscope: a "pulse train" wherein the pulse repetition frequency is indicative of the magnitude of the transmitted signal. The absence of a pulse train can also cause a reaction, explaining why amputees still feel parts of the body that no longer exist.

The meaning of the individual signal to the body's nervous system is dependent on where pulse train appears. The brain consists of regions that handle various neural functions and provide input for thoughtful and sensory processing. The peripheral nervous system contains axons that serve as communication channels and repeaters between the sensory nerve endings and the spinal cord and ultimately the brain. The neuromuscular system also consists of axons that communicate in the opposite direction allowing the brain to cause various muscle motions. Axons are grouped together into multi-channel peripheral nerves as they approach the spinal cord or the brain. Some axons are myelinated to increase the propagation rate of the pulse trains to and from the extremities of the body.

Neuromodulation devices strive to create, negate, or alter these naturally-occurring pulse trains in a targeted location to achieve a beneficial result. This may include blocking or stimulation of neural activity. Ultimately, an electric field is required at the location that causes ions to appropriately to trigger an action potential that then can propagate unassisted through the nervous system to its destination. This electric field may be induced rather than generated directly. For example, traditional magnetic stimulation first creates a time-varying magnetic field from a coil of wire, which in turn generates an electric field per Faraday's law. When this electric field is induced on a portion of the neurosensory system, or the neuromuscular system, or brain's neural network, it can alter that system by depolarizing or hyperpolarizing the pulse trains that naturally exist or by inserting a pulse train that does not exist. In the nervous system and the brain, these pulse trains run continuously; only the frequency changes to convey the intensity information.

The prior-art neural stimulation devices fall into three categories: (1) implanted wire stimulation wherein electrodes implanted at a targeted location and connected by wires to a driver circuit possibly also implanted in another part of the body, (2) magnetic stimulation wherein changing magnetic fields produced by a coil outside the body generate electric fields inside the body that alters the natural nerve or neuronal signals, and (3) skin-electrode stimulation wherein electrodes are placed on the skin and cause current to flow into the body from one electrode to the other. Deep Brain Stimulation (DBS) is an example of implanted wire stimulation. Transcranial Magnetic Stimulation (TMS) is an example of magnetic stimulation. Transcutaneous Electrical Neural Stimulation (TENS) and Electro Convulsive Therapy (ECT) are examples of skin-electrode stimulation.

Implanted wire stimulation is highly targeted, but also highly invasive and unstable due to electrode movement from wire-tugging during bodily motions. Infection is also a disadvantage especially if the driver circuit is not implanted. The mechanism of action is increasing or decreasing the frequency of natural action potentials and therefore well understood. Examples of implanted wire stimulators include the Vagus nerve stimulator offered by Cyberonics and covered in U.S. Pat. No. 8,571,654B2 that has helical electrodes, and US2016/0175600A1 where the implant includes a battery charged wirelessly by external coils transmitting the recharge energy magnetically. Some implanted wire stimulators have implanted micro-coils that induce electric fields in the body instead of providing voltages on electrodes, such as US2015/0080637.

Magnetic stimulation is non-invasive, but unpredictable and low in efficacy because the stimulation is not targeted and the mechanism of action is not understood. Regarding medical treatment, magnetic stimulation has achieved regulatory approval for treating major depression, neuropathic pain, and headaches. According to clinicaltrials.gov, 1165 clinical studies have been or are being performed with "magnetic stimulation" by 427 unique sponsors to understand its effect on 450 different conditions. Magnetic stimulation may include a single external coil, multiple external coils for better targeting such as US2012/0302821A1 and also wearable coils such as U.S. Pat. No. 9,072,891B1 and US2010/0160712A1.

Skin-electrode stimulation is non-invasive, but untargeted and uncontrollable because the electrical current follows multiple paths with varying intensity. The mechanism of action of skin-electrode stimulation is not understood except for ECT where an electrical jolt is large enough to intentionally produce a full seizure in the brain. ECT and TENS are approved for very few indications and efficacy is low.

SUMMARY

The number of approved treatments are minimal today and the efficacies are very low despite decades of costly research for general magnetic stimulation. Many research papers blame the lackluster progress on limitations of the state-of-the-art apparatus for magnetic stimulation, including the following: (1) lack of targeting of stimulation location (2) premature over-heating of the coils, (3) inability to penetrate deep into the body, (4) loud noises disturbing the patient, (5) inability to pre-test on small animals because small coils overheat very quickly, and (6) inability to define a credible placebo process.

The effect of the prior-art magnetic stimulators when applied to the brain is called a "virtual lesion" in the sense that all these stimulators can do is temporarily disable a portion of the brain's communication system. Interruption of a patient's speaking is an often-demonstrated manifestation of the virtual lesion via magnetic stimulation. Because the prior art is not able to precisely create the natural pulse trains that the mind or body expects, the effect of stimulation is not predictable and often not repeatable. The stimulation intensity is limited by the prior art to a transient and narrow range between no-effect and damaging-effect. What is really needed is a lower but continuous intensity, but the overheating of the prior-art stimulators prevents this type of protocol.

The first problem with the prior art magnetic stimulation coils is that they overheat prematurely. But, to maintain the expected and predictable response, the stimulation must occur continuously. Magnetic stimulators of the prior art are limited to a few seconds of stimulation followed by a long and necessary period of cooling down of the coil. If the electrical current in the prior-art coils was reduced to prevent overheating, the induced pulse trains would be too weak to have an effect. For this reason, the prior-art systems are over-driven for short periods of time between coil cool-downs.

Because of the overheating problem, the devices on the market configured to automatically turn off when the heat limit is reached. For example, a stimulator may require 20-60 seconds of cool-down for every 2-10 seconds of stimulation. In addition, this researcher showed directionally that more sessions led to greater remission rates of depression. Continuous and appropriate intensity levels of stimulation, along with better targeting, is likely to be far superior to the interruption constraints of the prior art stimulators.

A second problem with prior art magnetic stimulation is that inducing an electric field strong enough to evoke an action potential even a few centimeters away from a coil is not trivial. The prior-art coils must have thousands of amperes of electrical current that appears and disappears in about 100 microseconds, which is the rise time of an action potential. The coils have inductance, which further requires a high-voltage power supply to change the current quickly. This supply is connected to the coil for about 100 microseconds, and then is disconnected abruptly. The high voltage is required to change the current in coil quickly, and the high amperes in the coil are required to induce a sufficient electric field in the body that achieves or alters an action potential.

For example, the coils in the apparatus available from MAGSTIM, INC. (Morrisville, NC) need 5000 amps of current to appear and disappear from the coil in about 100 microseconds. In order to achieve this, a power supply of thousands of volts is used. In order for this system to create a continuous pulse train requires kilowatts of power, which will easily overheat the coil and the electronics that drives the coil.

The following patents or patent applications use this method of switching on a high voltage power supply to a coil, then switching it off before the coil overheats in order to allow it to cool down: US20080306326A1, U.S. Pat. No. 6,179,770B1, US20120108883A1, U.S. Pat. Nos. 6,527,695B1, 5,743,844A US20070293916A1, and U.S. Pat. No. 8,545,378B2. In these prior patents and patent applications, a capacitor is charged to a very high voltage, then a transistor connects this high voltage to the coil briefly to create a magnetic pulse, which by Faraday's law, induces an electric field pulse in the body. The transistor repeats this operation to create multiple pulses, then stays off to let the coil cool down.

These prior art coil-driver circuits either make no attempt to recycle the magnetic energy of the coil or merely do so by allowing it to flow back into the high-voltage capacitor, such as described in US20090018384A1.

The huge amount of current flowing in and out of the prior-art magnetic stimulator causes a knocking noise that is loud enough to seriously disturb a patient. The coil acts like the voice coil in a speaker, thereby creating sounds from the pulsed magnetic forces acting on the coil itself or any ferromagnetic materials nearby.

The prior art magnetic stimulator also renders impossible a placebo control group because the noise generated allows the human subjects to distinguish the true treatment from the silent or quieter "sham" treatment.

A third problem with the prior art magnetic stimulator is that they do not scale down well to smaller coils for small-animal testing because the smaller coils overheat faster than the larger coils designed for humans. Hence, animal testing is very difficult.

A fourth problem with prior art magnetic stimulators is that they require thousands of volts and thousands of amperes to create a pulse train for a too-short period of time and already. Even then, the action potentials can only be produced about 1-2 centimeters into the body for a short period of time. Penetrating deeper into the body would require larger coils with higher inductance, and hence even higher voltages and/or current. This severe power requirement has limited magnetic stimulation to nerves, axons, and neurons close to the surface of the body.

Clearly, then, improvements are needed in prior-art magnetic stimulators for magnetic stimulation to become a viable, predictable, pervasive, efficacious, and cost-effective mechanism for health care and for research.

The invention described herein addresses all mentioned limitations of prior-art magnetic stimulation, skin-electrode stimulation, and implanted wire stimulation. Hence, this invention is expected to greatly advance the state of the art of magnetic stimulation for the benefit of mankind.

In one embodiment, a wireless neuromodulation system is provided to allow wireless stimulation to (1) be targeted to an area as small as a single node on a neural pathway or a single neuron in the brain, (2) work with readily available power supply voltages, (3) work with larger and smaller stimulating coils in order to reach deeper into the human body and to enable small-animal studies, respectively, (4) be wearable and powered with small batteries, (5) dramatically reduce the noise produced by the coil(s) when activated, (6) allow for a placebo control group by making the sham and active systems less distinguishable, (7) to allow the stimulating coil to be driven continuously without overheating, (8) reduce the invasiveness to a single injection at the desired location of stimulation, and (9) make the injectable piece so small that it will not move around over time in an active human body. All these objectives are achieved with this embodiment, greatly improving the state of the art of neural stimulation.

The neural stimulator described herein may use an external coil to produce changing magnetic fields outside the body, as in traditional magnetic stimulation, in conjunction with one or more tiny injectable objects that concentrates the induced electric field to a highly-targeted location. These systems also add a driver circuit for the magnetic coil that allows for high voltage and fast pulses in the coil, while requiring low-voltage power supply that could be a wearable battery. The coil and driver circuit are also small enough to be easily wearable.

Miniaturization of the magnetic generator may be achieved using (1) an efficient driver circuit that enables thousands of volts in the coil from a low voltage battery, (2) a non-invasive, injectable electric field concentrator that targets the stimulation to an area measured in microns, and/or (3) a fast rise time in the current of the coil that induces a large electric field to evoke an action potential. Each of these features may provide an advantage in coil power of 10 to 100×, making the total benefit over 1000×. For example, where a TMS device would require 10,000 instantaneous watts of electrical power in the coil to stimulate a portion of the body, these systems requires less than 10 watts. This power level reduces the size of the coil, the driver circuit, and the battery to easily wearable sizes.

Some of the systems disclosed herein use an electronic circuit to drive the stimulator coil or coils by stimulating a pulse as a partial cycle, half cycle, full cycle, or multiple cycles of a resonance of the stimulator coil combined with a capacitor. Once the desired cycle(s) of the resonance are complete, the circuit remains in a quasi-steady state or turned off until the desired time for the next pulse.

By using this approach, the inductive energy of the stimulating coil is recycled through the capacitor, and therefore not wasted on each cycle. In addition, the voltage across the capacitor can reach hundreds or thousands of volts even when the supply voltage is very low. This high voltage internal to the capacitor is then used to rapidly change the current in the stimulating coil for the next pulse. The recycling of the inductive energy also allows for the stimulating coil to have more turns, and therefore needs less current flow to create the same magnetic field strength. The preferred embodiment can create the needed magnetic field pulses with power supply in the range of 3 to 45 volts DC (vs. >10,000 volts for the prior art magnetic stimulation) and an average current flow of 0.2 to 3.0 amps (vs. 5000 amps for the prior art). In the preferred embodiment, the stimulating coil has many times the number of turns as the prior art coil for traditional magnetic stimulation.

In some embodiments of the systems, the healthcare provider or the user/wearer is able to (1) set the amplitude of the stimulating pulses by adjusting the supply voltage, (2) set pulse width by selecting the appropriate capacitor, (3) set the burst frequency and number of resonant cycles per burst by using a programmable digital pulse generator, (4) reverse the polarity of the stimulation by reversing the leads connecting the stimulating coil, (5) introduce asymmetry and control the subsequent undershoot by adding ferromagnetic metal to the core region of the coil or by adding a resistor in series with the coil or by changing the pulse width from the pulse generator to be less than one resonant cycle, (6) achieve a desired penetration depth by sizing the diameter of the coil, and/or (7) set the duration of the stimulation session by turning the system on and off. Hence, many key parameters are easily tuned to implement or derive the clinical or therapeutic protocol for neural stimulation. The electronic components mentioned above may be controlled by a microprocessor or computer to achieve pre-programmed stimulation protocols.

In one embodiment, a neuromodulation system may be provided, comprising at least one elongate conductor configured for placement inside the body with one end adjacent to the site to be stimulated, and a magnetic field generator configured to be placed outside the body and to generate a time varying magnetic field perpendicular to a longitudinal axis of the conductor. The elongate conductor may comprise a material selected from a group consisting of a metal, a resistor, and carbon fiber. The metal may be copper, tungsten, chromium, steel, stainless steel, nickel, nichrome, titanium, gold, silver, brass, or any alloy thereof. The elongate conductor may be coated with at least one of protective layer and insulating layer. The protective layer may comprise PTFE, nylon, silicone, polyethylene, polyurethane, latex, polyimide, BoPET, or any combination thereof. The elongate conductor may be configured for placement adjacent to a peripheral nerve, spinal nerve, brain-stem nerve, or brain neuron or other neuron or axon. The elongate conductor may comprises a cylindrical shape with a diameter and a length, wherein the diameter may be less than the length. The elongate conductor may be a monolithic structure with no curves or angled bends along its longitudinal axis. The elongate conductor may comprise a wire segment or strands of wire segments, for example. The elongate conductor may be injected into the body through a guiding tube, such as a needle of a syringe or other implantation device. The magnetic field generator may comprises a coil, the coil comprising one or more coil windings of wire. The magnetic field generator may be connected in parallel with a capacitor and configured such that a stimulation signal may generated, result from, or defined by a portion in time of a resonance between the coil and the capacitor. The parallel capacitor and coil may be configured to be activated by a DC power supply on one side and a switch to ground on the other side, wherein a time period between the switch opening and switch closing determines the portion of the resonance that becomes one or more stimulation pulse or pulses. The switch may be a combination of a transistor and a rectifier and a switching action may be configured to occur by turning the transistor on or off by applying a voltage to a gate or a base of the transistor. The switching action may be configured to open at a beginning of a first full resonant cycle and close prior to an end of the first cycle, at the end of the cycle, at an end of multiple cycles, or within a later cycle. The switch may be configured to turn off the gate or base of the transistor just prior to a series of decaying resonant pulses and then turned on to build up the current in the stimulator prior to the next decaying series to save electrical energy consumed by current in the coil between pulse series. The parallel capacitor and coil are activated by an H driver with four switches. Each switch may comprise a transistor and a rectifier. In some further embodiments, a first two of the four switches are configured to open and the other or second two of the four switches are configured to close at the beginning of a first half of a resonant cycle and at the end of a second half of the resonant cycle, the first two switches are configured to open and the second two switches are configure to open. The magnetic field generator may comprise a stimulator coil, the stimulator coil comprising a material with high magnetic permeability configured to contain the fringe fields. The material with high magnetic permeability may comprise rigid or flexible ferrite, steel, or iron. The coil may further comprise a conducting ferromagnetic material that reduces the amplitude of subsequent resonant pulses relative to the prior pulses. The material may comprise iron, cobalt, nickel, steel, or an alloy or other combination thereof. The one or more coil windings may be in a plane or multiple adjacent planes, The one or more coil windings may comprise magnet wire. The one or more coil windings may comprise metal deposited on a layered substrate. The substrate may be rigid, and may optionally comprise FR-4 glass-reinforced epoxy laminate, glass, or hard plastic. In other embodiments, the substrate may be flexible. The flexible substrate may comprise polyimide, BoPET, polyethylene, polyurethane, nylon, or PTFE. The system may further comprise one or more of a microprocessor, rechargeable battery, user interface, physician interface, nurse interface, data storage, and network connection. The network interface may be configured to monitor or control the stimulator by a computer, by the user, or by a professional or to gather data or statistics therefrom. The elongate conductor may comprises a monolithic body, and may lack a battery, may lack feedback circuitry, and/or may lack power management circuitry. The elongate conductor may comprise a discrete metal wire with a diameter of less than 100 microns. The elongate conductor may comprise a first end, a second end, a body therebetween, and has a length of 10 mm or less from the first end to the second end, and may be configured such that neither the first end, the second end, or the body may be connected to another conductor, and/or include any curves or bends along a longitudinal length of the conductor.

In another embodiment, a method of treating a condition is provided, comprising identifying a patient with one or more implanted elongate conductors, placing a coil of an external magnetic field generator against a surface of a treatment site of the patient, and applying a magnetic field to the one or more implanted elongate conductors to generate therapeutic neural stimulation. The method may further comprise activating the magnetic field generated to, modulate, increase or decrease action potential activity at the treatment site. The action potential activity may be located in neurons in the brain, sensory system, or neuromuscular system. The method may be used in the treatment of a pain disorder, mental disorder, sensory disorder, or muscular disorder, and the pain disorder may be due to amputation, neuropathy, nerve damage, or injury. The mental disorder may be depression, Huntington's disease, Alzheimer's disease, dementia, anxiety, insomnia, post-traumatic stress disorder, and/or panic attacks. The method may further comprise generating the magnetic field using less than 100 peak amps and 100 volts of peak voltage.

In still another embodiment, a treatment device is provided, comprising a syringe or injector body, a sliding plunger or pushrod located in the syringe or injector body, a needle attached to the syringe or injector body, and at least one discrete elongate conductor located in the syringe or injector body, wherein the syringe or injector body and needle restrain the orientation of the at least one elongate conductor, and wherein the elongate conductor comprises a monolithic metal body with a diameter of less than 100 microns. The monolithic metal body may have a length of less than 10 mm.

In another embodiment, a neuromodulation system is provided, comprising at least one elongate conductor with a length of less than ten millimeters and a transverse dimension to the length of less than one millimeter, configured for implantation adjacent or against a nerve, axon, or neuron, and a magnetic field generator that may be spaced apart from the at least one elongate conductor, and configured to generate an induced and concentrated electric field at the at least one elongate conductor. The at least one elongate conductor may be pre-loaded in an injection device and in a sealed sterile package. The at least one elongate conductor may be a plurality of elongate conductors positioned serially or in parallel within the injection device. The magnetic field generator may further comprise a rechargeable battery. The magnetic field generator may be located in a housing comprising at least one of an adjustable strap, elastic band, hook-and-loop connector, buckle, adhesive, or pin, that is configured to attach the housing a location on a human body or in attire or pockets thereof worn by the human body. The housing may have a height relative to a skin surface at the location on the human body that may be less than one centimeter.

In another embodiment, a method of treating a patient is provided, comprising inserting at least one elongate conductor against or adjacent to a nerve, axon, neuron or neural tissue, wherein the conductor has a length of less than ten millimeters and a transverse dimension to the length of less than one millimeter, positioning a magnetic field generator at a location spaced away from the at least one elongate conductor, and using the magnetic field generator to provide an induced and concentrated electric field to at least one elongate conductor. The magnetic field generator may be an ambulatory magnetic field generator comprising a housing with a plurality of magnetic coils, a driver circuit, and a rechargeable battery. The plurality of magnetic coils has a net thickness of less than three centimeters. The at least one elongate conductor may be against a skin surface. The method may further comprise maintaining the location of the magnetic field conductor using at least one strap, elastic band, hook-and-loop connector, buckle, adhesive, pin, or pocket.

In one embodiment, a magnetic stimulation system is provided, comprising an external coil stimulation system configured for use against a tissue surface of a patient, and to generate a therapeutic magnetic field during therapy using at least one of 100 peak amps or less of instantaneous current, and a power supply voltage of 100 peak volts or less. The external coil stimulation system may be configured with an amperage limit of 100 amps or less of instantaneous current. The external coil stimulation system may be configured with a voltage limit of 100 volts or less. The external coil stimulation system may be connected in parallel with a capacitor such that a stimulation signal may be a portion in time of a resonance between the external coil stimulation system and the capacitor. The parallel capacitor and external coil stimulation system are configured to be activated by a DC power supply on one side and a switch to ground on the other side, wherein a time period between the switch opening and switch closing determines the portion of the resonance that becomes one or more stimulation pulse or pulses. The switch may be a combination of a transistor and a rectifier and a switching action may be configured to occur by turning the transistor on or off by applying a voltage to a gate or a base of the transistor. A switching action of the switch may be configured to open at a beginning of a first full resonant cycle and close prior to an end of the first cycle, at the end of the cycle, at an end of multiple cycles, or within a later cycle. The switch may be configured to turn off the gate or base of the transistor just prior to a series of decaying resonant pulses and then turned on to build up the current in the stimulator prior to the next decaying series to save electrical energy consumed by current in the coil between pulse series. The parallel capacitor and coil may be activated by an H driver with four switches. Each switch may comprise a transistor and a rectifier. A first two of the four switches may be configured to open and the second two switches of the four switches may be configured to close at the beginning of a first half of a resonant cycle, and wherein the first two switches are configured to close and the second two switches are configured to open at the end of a second half of the resonant cycle.

BRIEF DESCRIPTION OF THE DRAWINGS

FIG. 4a is a schematic representation of an injectable elongate conductor positioned and oriented on a peripheral nerve; FIGS. 4b-4f show cross-sectional views of various positions and orientations of the injectable(s) relative to a nerve, or group of nerve fibers;

FIG. 6a depicts a prior-art implanted wire stimulator for deep brain stimulation; FIG. 6b an exemplary embodiment of a wireless neuromodulation system an injectable conductor at the same location as the prior-art electrode tips in FIG. 6a, in combination with a wearable magnetic field generator;

FIGS. 23a to 23f illustrate how the injectable conductor is placed near a nerve of the a part of the body with an injection from a syringe;

FIG. 29 shows the oscilloscope tracing of action potentials of the sensed neuron when the stimulator is turned on;

DETAILED DESCRIPTION

Figure 1A:
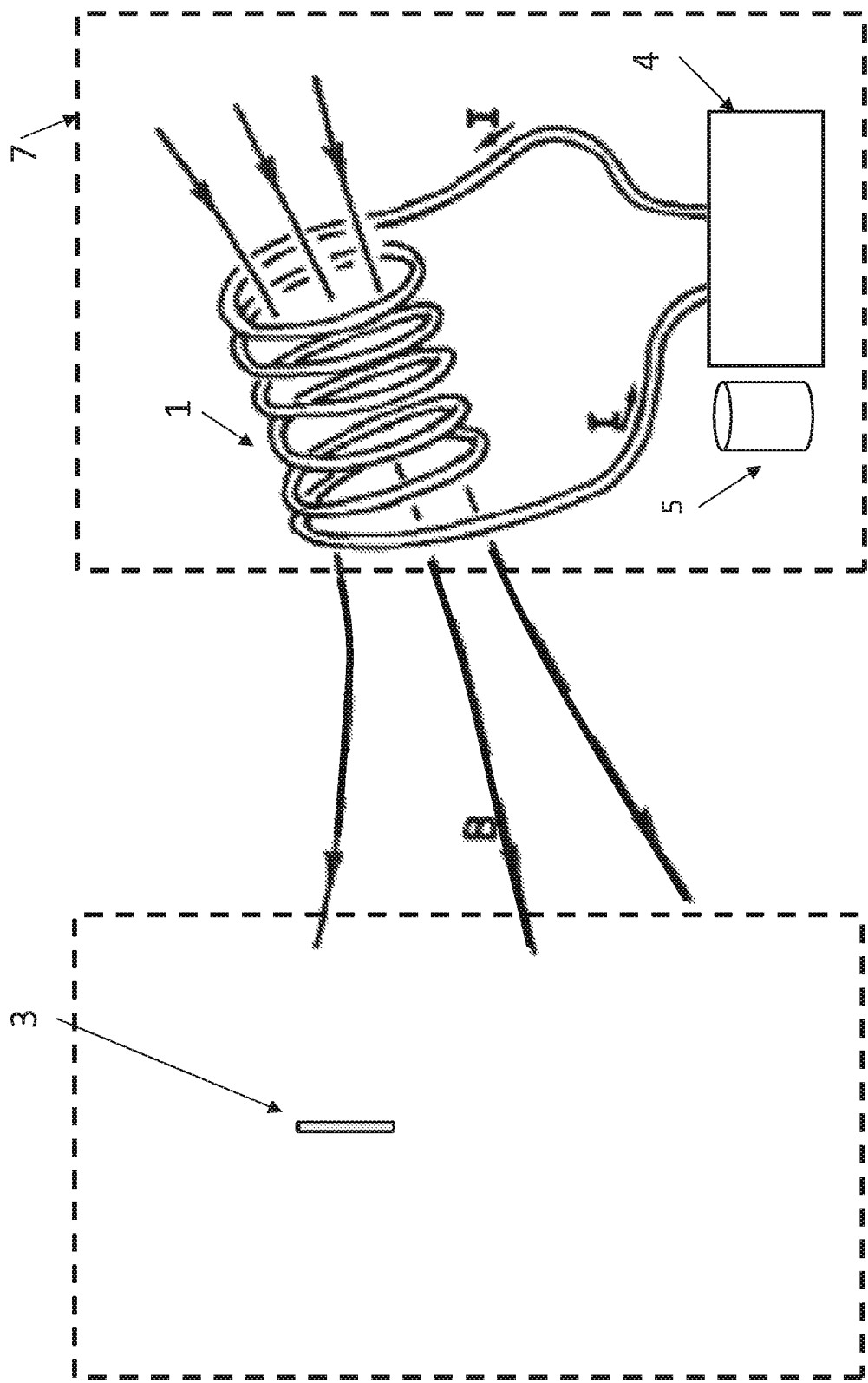
FIG. 1a is a schematic representation of a wearable stimulator coil which is pulse-driven by a driver circuit, using an injectable elongate conductor that concentrates the electric field induced by the coil's changing magnetic field.

One exemplary embodiment of this neural stimulation system comprises an external or wearable portion containing a magnetic field generator that may be coupled to the external surface of the patient, and an internal or implanted injectable portion that concentrates the electric field of the stimulator to activate only a targeted a nerve fiber or neuron or group of nerve fibers or neurons. As depicted in FIG. 1a, the neuromodulation system 7 comprises a wearable portion 3 comprises a stimulator coil 1 that is driven by a driver circuit 4 and powered by a battery 5 and/or other power source. The driver circuit 4 may contain a processing or computer unit to generate the drive signals to the stimulator coil 1 and to receive input to allow for adjustments in stimulation parameters from the user or healthcare provider, via an interface to a smartphone or other device, over a WiFi, Bluetooth, RFID, or similar network or wireless protocol, at the location of the user or from a remote location. The wearable portion 7 is attached to the body by straps, elastic bands, Velcro, buckles, adhesives, pins, or similar mechanism, with the stimulator coil(s) facing the skin. Alternatively, the wearable portion may be attached to clothing or other attire using pockets, clamps, pins, adhesives, Velcro, or other suitable attachment means. Within the clothing or attire, the appropriate location of the wearable portion depends on the location and type of stimulation.

The current flowing in the stimulator coil 1 of FIG. 1a produces a changing magnetic field that easily penetrates deeply into the body, including the hard and soft tissue. This changing magnetic field, by Faraday's law of electromagnetics, induces an electric field that is concentrated in one or more injectable portion or components 3 that also penetrates the body. In the some embodiments, this induced electric field is may be configured to generate with a larger area effect, or a smaller localized effect to alter the body's neurological system except at the immediate location of the injectable conductor 3. The changing magnetic field from stimulator coil 1 induces an electric field which moves the free electrons in the injectable conductor 3, causing one end-point to be positively charged while the other end is negatively charged. This induced voltage between the endpoints of the injectable conductor 3 then acts like two electrodes placed at the endpoint locations and activated with a voltage. This activation moves ions near the tip of injectable conductor 3 and evokes an action potential or stream of action potentials at nearby neuron(s) or axon(s) if the tip voltage is sufficient to raise the resting potential to beyond the trigger potential.

A wide variety of coils may be used with various embodiments of the neural stimulator. The number of turns can vary from 20 to 300, or about 40 to about 200, or about 10 to about 150, or more. More turns increase the inductance of the coil, which increases the voltage rating of the transistors and rectifiers in the driver circuit, but lowers the current required to produce a given magnetic field.

The diameter of the coil turns is may be selected based on the penetration depth needed for stimulation. In some embodiments, the diameter of the coil is approximately four times the penetration depth required. Some nerves are within 1 cm of the skin surface, making a 4 cm diameter coil about the right size. Other stimulation locations such as within the spinal cord of an obese person could be 10 cm deep, making the optimal coil diameter around 40 cm for the lowest power consumption. In this case, a smaller coil driven with more power might be more practical. Unique coils such as H coils and figure eight coils have been shown to generate a stronger or more concentrated magnetic at a certain penetration depth, and these coils could be advantageous to use with this stimulator. In some variations, the coil diameter (or average transverse dimension) is then in the range of about 2 cm to about 50 cm, or about 3 cm to about 40 cm, or about 4 cm to about 25 cm.

The diameter of the wire used within the coil determines the electrical resistance of the coil and hence how much heat it generates given the amount of current required to generated the needed magnetic field at the injectable location. Smaller diameter wires generate more heat than larger diameter wires, but larger diameter wires add more weight to the wearable portion of the stimulator. In most embodiments, the diameter of the wire is between 0.3 to 2.3 mm in diameter, with the smaller diameter typical for lower penetration depths. In other embodiments, the wire diameter or width may be in the range of about 0.5 mm to about 3 mm, or about 0.4 mm to about 2.5 mm, or about 0.2 mm to about 3 mm.

The coil for the neural stimulator may be configured to generate a magnetic field strength between 0.001 and 0.1 Tesla to induce a sufficient voltage at the injectable to stimulate action potentials. The magnetic field strength may be smaller for narrower pulse widths because the induced voltage is proportional to the time derivative of the magnetic field. In contrast, prior-art TMS systems require magnetic field strengths of 1-5 Tesla because the induced electric fields not concentrated by an injectable as described herein. The magnetic field strength described herein can be achieved with coil currents of 2 to 20 amperes instantaneous during pulse bursts and 0.2 to 5.0 amperes average in embodiments that turn off between bursts. In contrast, prior art TMS systems require hundreds or thousands of amperes instantaneous coil current.

The pulse width, burst rate, leading pulse amplitude, and leading pulse polarity (polarizing or depolarizing of the axon or neuron) are defined by the stimulation protocol and are typically the same for this Neural Stimulator as required for prior-art wired electrode systems, subject to the resonant characteristics of this stimulator. Typically, the pulse widths are 20 microseconds to 1 millisecond, the burst rates are 10 Hz to 200 Hz. The leading pulse amplitude of prior-art wired electrodes typically generates 10 microamperes to 1500 microamperes of polarizing or depolarizing current, but the actual current needed at the axon or neuron is 10-20 microamperes. Larger currents are needed because of dispersion, that may results from the electrodes not being positioned close enough to the axon or neuron, or if there is a significant myelination or perineurial layer between the implant component and the axon or neuron. In this Neural Stimulator, the injectable is placed as close as possible to the nerve, nerve bundle, nerve fiber, or neuron to be stimulated. Hence, the current produced by the injectable is 10 to 50 microamperes, which in turn requires 20 to 100 millivolts between the endpoints of the injectable for myelinated peripheral nerves or 10 to 20 millivolts for unmyelinated axons or neurons. Depending of the length of the injectable, the electric field strength needed at the injectable is between 1.0 volts/meter for 10 millivolts coupled with a 10 mm injectable, and 100 volts/meter for 100 millivolts coupled with a 1 mm injectable.

The leading stimulation pulse may be repeated within bursts of pulses. Often, it is desired for each burst to contain both positive and negative pulses to avoid charge buildup in the nervous system. Multiple bursts of stimulation generally cause the body to generate multiple action potentials.

Action potentials of the human body are typically pulse-frequency modulated, meaning that the intensity of the signal is determined by the repetition rate. Hence, the driver circuit 4 in FIG. 1 will repeat the stimulation burst at the desired repetition rate. In many therapies and applications, it is not necessary for the stimulated voltage waveforms to mimic the body's action potential waveform, because the body produces its own action potentials in response to a variety of stimulation pulse shapes from the stimulator. However, pulses that are too short in time may not stimulate the nerve and pulses that are too long in time may not achieve the burst rate required for the desired effect.

Referring back to the exemplary neuromodulation system in FIG. 1a the neural stimulator may be characterized as a transformer, wherein the injectable conductor 3 is a like a secondary winding having a fraction of a turn. For example, the induced voltage in the injectable conductor 3 may be characterized as a fraction l/L of the induced voltage in a single-turn induction coil 2, of FIG. 1b where l is the length of the injectable 3 and L is the length of the single-turn induction coil 2. This relationship is one way to determine the induced voltage at the injectable conductor 3, which is otherwise difficult to measure.

Another consideration of the function of injectable conductor 3 of FIG. 1a is as an electric field concentrator. Any elongate conducting object will naturally concentrate the electric field surrounding it as illustrated in FIG. 2a, FIGS. 2b-2f shows an elongate straight conductor in the shape of a cylinder which comprises the injectable conductor 3, and this conductor could have an insulating layer, or not, with conducting portions exposed on each end. Note that the injectable conductor 3 in FIG. 2b of the could be a segment of the long wires used in implanted stimulators. These wires are already available on the market and have already been tested to be safe inside the human body for extended periods. In the depicted embodiment, the cross-sectional shape of the conductor along its length is uniform, but in other examples, the cross-sectional shape or size may vary along its length. In other examples, the conductor may have an arcuate shape or one or more angular bends.

Figure 1B:
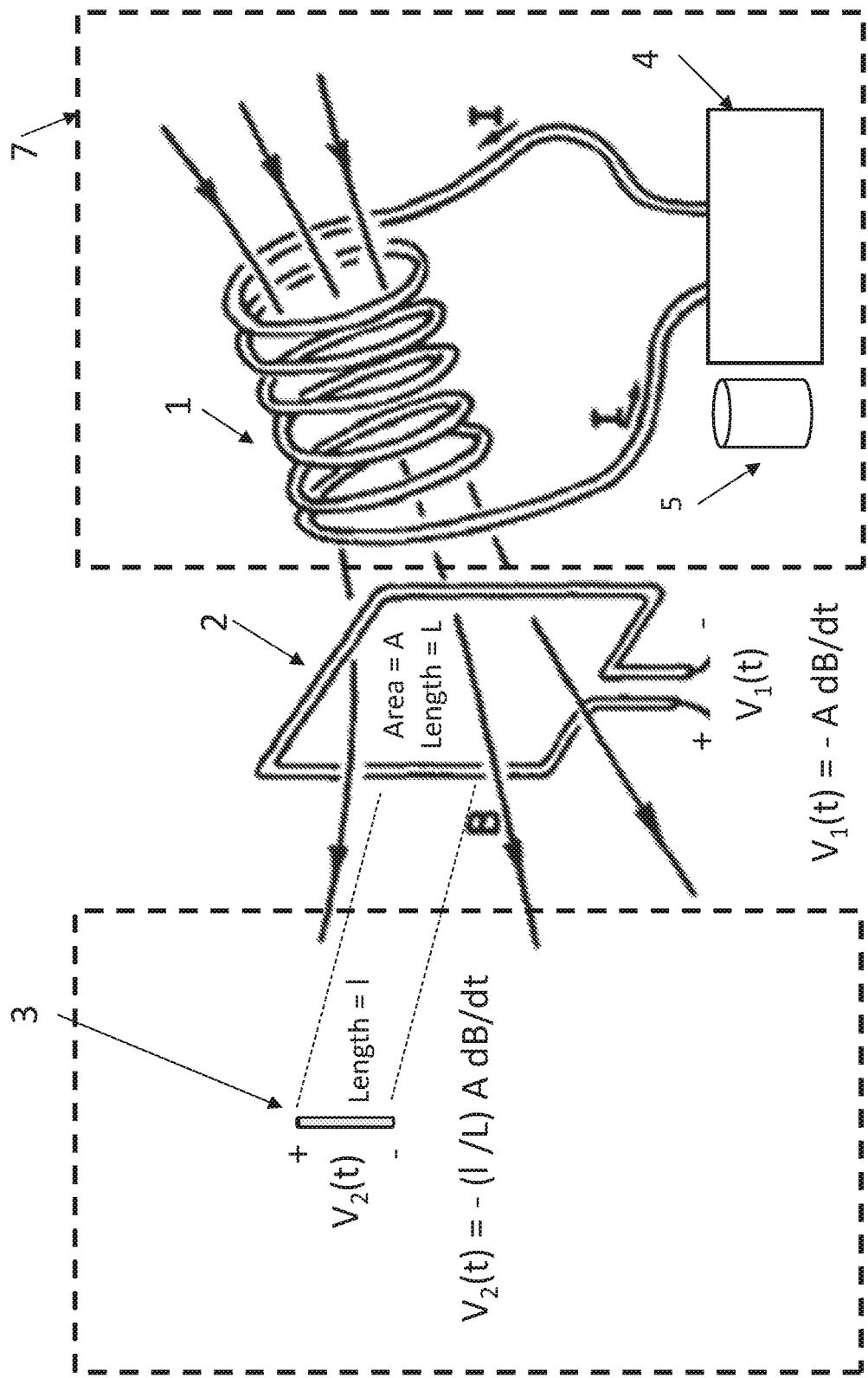
FIG. 1b illustrates how the elongate injectable acts as a fraction of a turn in a secondary coil.

The amplitude of the induced voltage $V_2(t)$ produced by the stimulator coil 1 in FIGS. 1a and 1b is proportional to the length l of the conductor by the formula $V_2(t)=(l/L)*A*dB/dt$, where L is the length of the single-turn induction coil. A is the cross-sectional area of the single turn induction coil. The area A of single turn induction coil 2 in FIG. 1b is $(L/4)^2$. B is the magnetic field produced by the stimulator coil, which is, in turn, proportional to the electrical current flowing in the stimulator coil.

The cross-sectional dimension of the stimulator coil L/4 is typically between 1 and 20 cm, which needs to be small enough to be comfortable as a wearable, but also have a penetration depth to reach the injectable conductor. Some stimulation sites for the injectable like the Vagus nerve are within 1-2 cm, but other stimulation sites like the spinal cord could be 20 cm deep for an obese patient.

The length of the injectable conductor from a first end to a second end is typically between 1 and 10 mm. The conductor is separate, the first end, the second end, or the body of the conductor not attached to any other conductor structure, but may be optionally coated with a material as described herein to modulate the biocompatibility of the conductor within the body of a patient. In some variations, the conductor is straight, with no curves, angled bends or branched segments. In other variations, the conductor may have a curve or angled bend region, but wherein the curb or angle is angled no more than a total of 5 degrees, 10 degrees, 15 degrees, 20 degrees, 25 degrees, 30 degrees, 35 degrees, 40 degrees or 45 degrees. In some examples, lengths in this range may be long enough to produce sufficient induced voltage to stimulate but short enough to not cause complications in the body such as displacement from bodily movement, feeling of discomfort, and interference with surrounding tissue. In some cases, the injectable could be as long as 100 mm if it is located in the chest or spine. A longer injectable generates a higher induced voltage at the endpoints, which may provide lower power and longer battery life for the wearable field generator. In other examples, the conductor may have a length of about 2 to 30 mm, 4 to 20 mm, or about 3 to 15 mm. The diameter or transverse cross-sectional dimension relative to the longitudinal axis of the injectable conductor is typically between 8 and 50 microns, which is thick enough to apply a voltage over a sufficient area of the nerve or neuron and be physically strong enough to not bend during normal activity of the body, but also be thin enough to be injectable through a syringe or other injection device. These thin injectables are effective for highly targeted stimulations for single nerve fibers or small groups of fibers or neurons. For large nerve bundles and for muscle stimulation, the cross section of stimulation should be large, and in these cases the injectable could have a diameter of up to 4 mm and still be accommodated by standard gauge syringe needles.

As noted previously, certain embodiments of the neural stimulator only utilize an injectable device, i.e. a small and very thin cylindrical device that can be placed by a syringe, making this system essentially minimally invasive. Prior art stimulators that require a coin, pill, or long antenna type implants require significant surgery to be placed inside the body, and these must be connected to a power source that is also located inside the body, which may require tissue dissection to implant the component(s). In other examples, a portion of a magnetic induction charger system is located inside the body and other part outside, requiring two coils with close spacing between them, like the stimulators available from Bioness (Valencia, CA). The RF-coupled devices from Stimwave (Pompano Beach, FL) uses RF coupling and require a long 45 cm antenna inside the body to reach the spinal cord area. Another RF-coupled wireless stimulator from Advanced Bionics (Valencia, CA) and described in U.S. Pat. No. 6,735,474 B1 has a smaller helical antenna, but the internal battery can only be recharged wirelessly when it is located very near the surface of the skin. RF coupling incurs losses when attempting to travel even small distances into the body. In contrast, certain embodiments of the neural stimulator described herein use magnetic coupling, reducing the size of the implanted portion considerably to be merely injectable. Due to their larger, heavier, and more complex configuration, existing implants tend to have more complications and potential problems. Their weight causes great shifts during bodily movements, and the long antennas or wires can be pulled out of place by natural bodily motion. In contrast, the small injectable devices of the embodiments of the neural stimulator are not heavy enough to be displaced with bodily motion, and not long enough to be susceptible to pulling out of place.

Figure 2A:
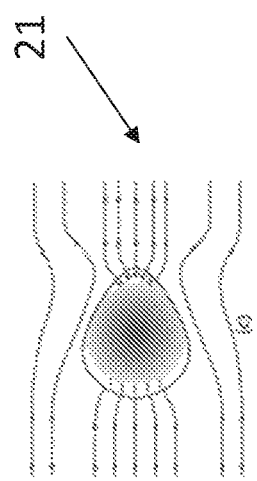
FIG. 2a is a schematic depiction of how an elongate conducting object can concentrate an electric field.
Figure 2B:
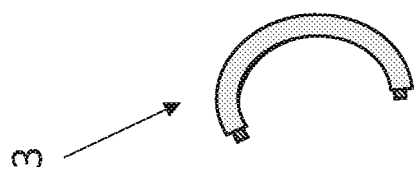
FIGS. 2b-2f depict exemplary elongate conductors insulated or not insulated that are sized to be injectable and small enough, if needed, to stimulate a single nerve, nerve bundle, or neuron or group of neurons.
Figure 2C:
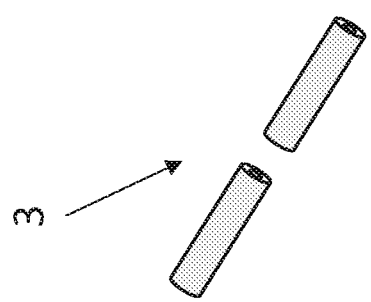
Figure 2D:
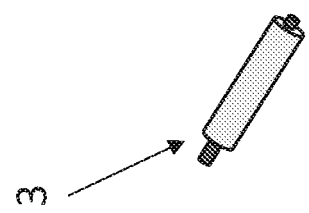
Figure 2E:
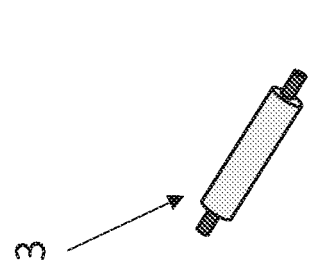
Figure 2F:
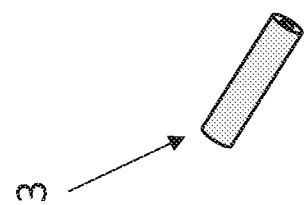

FIG. 2c shows an elongate straight conductor wherein the insulation is stripped off the same amount on each end. The surface area of the exposed conducting material determines the current density on the endpoints of the elongate conductor when activated by the field generator. By controlling the length of the stripped portion of the insulation, the current density exposed to the tissue can be controlled to avoid damaging the tissue while still achieving stimulation. FIG. 2d shows an elongate conductor wherein the insulation stripped off is different on one endpoint than the other endpoint. This difference can cause one end to have sufficient current density to trigger an action potential in the targeted nerve or neuron and the other end to have insufficient current density for stimulation for untargeted nerves or neurons. In large nerves or in the brain, there will likely be cases where the other endpoint of the injectable should not trigger action potentials to prevent side effects. Without limitation, the current density of one endpoint vs. another could also be achieved with different conductor diameter at each end in FIG. 2b, or by having a thicker or less conductive coating on one end vs. the other. The injectable could also be pre-formed into a curved or semi-circular shape, as illustrated in FIG. 2f. In this case, the injectable could be temporarily straightened while inside the syringe and then re-take this shape as it leaves the syringe, if at least one material comprising the injectable is elastic. FIG. 2e shows two injectables that generate an induced voltage between the two inner endpoints that is twice the voltage generated by one injectable. This configuration in FIG. 2e concentrates the current flow in the nerve or neuron very precisely between the two inner endpoints, allowing for better targeting and stronger stimulation.

The injectable conductor 3 could, without limitation, be copper, tungsten, chromium, stainless steel, nickel, nichrome, titanium, gold, silver, brass, any alloy of these, or any other conducting material. Or, the conductor may contain carbon, carbon fiber, or other resistive material in all or part, to limit the current flow to a safe level for human tissues. However, in some embodiments, the non-ferromagnetic materials may be used to reduce the potential interference with MRI diagnostics and because of magnetic attraction forces between the injectable and the magnetic field generator. Again, without limitation, the conductor could be partially or completely coated or insulated with PTFE (polytetrafluoroethylene), PET (polyethylene terephthalate), nylon, silicone, polyethylene, polyurethane, latex, polyimide, BoPET (biaxially-oriented polyethylene terephthalate), any mixture or combination of these, or other suitable insulator to protect the conductor from corrosion and/or to prevent the surrounding tissue from reacting adversely. The thickness of the insulation is typically 5 to 100 microns, thick enough to resist or avoid pinholes, scratches, or tears, but also thin enough to allow passage through a syringe or other injection device. The exposed conducting portion of the injectable conductor may be coated or plated with yet another conducting material is that more compatible with bodily tissue.

Figure 3:
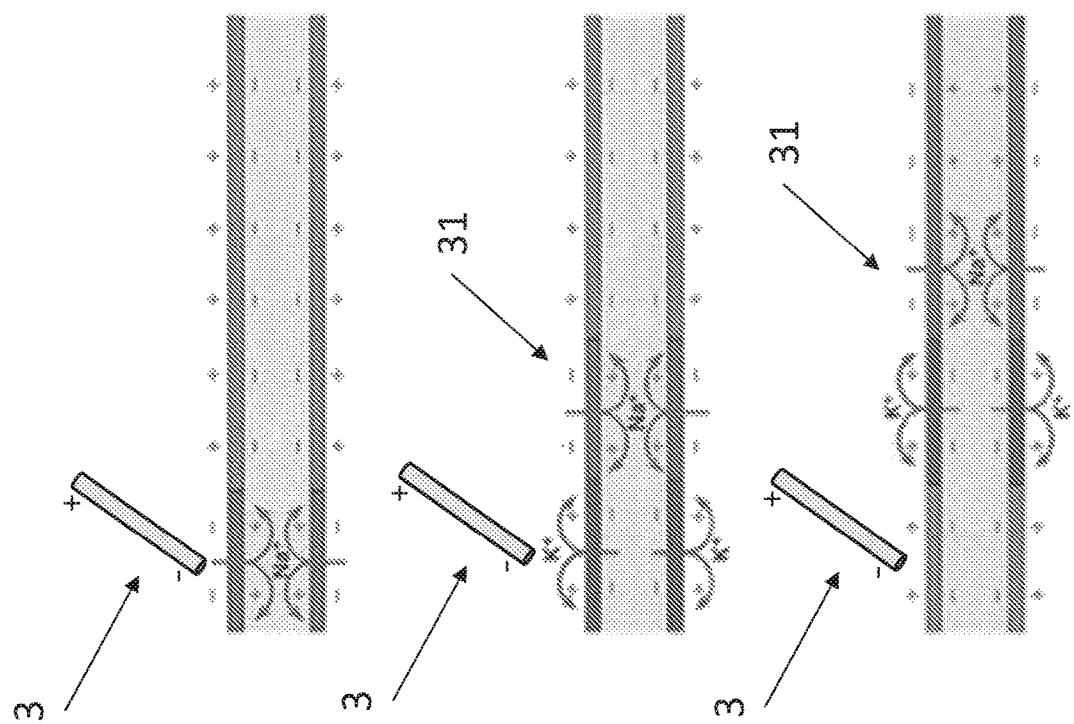
FIG. 3 is a graphical representation of the physical locations of the induced and concentrated electric field of the elongate conducting object located on a neural pathway to induce an action potential.

The injectable conductor 3 in FIG. 3 creates a voltage between each end, so placing one end near a nerve or neuron can stimulate action potentials. The pulse width, number of resonant cycles per burst, and burst frequency of this induced voltage is completely controllable from the wearable portion 7 of FIG. 1. This wearable portion can emulate the natural stream of action potentials, create bi-phasic and charge-neutral pulse shapes that have been shown to be benign, or achieve any other desired pulse shapes for the recommended stimulation protocol.

Furthermore, the injectable conductor 3 of FIG. 3 can be small enough in diameter or transverse cross-sectional shape to target a single nerve fiber or neuron, or be larger to stimulate a larger area possibly including more than one neuron or multiple nerve fibers or an entire nerve. Without limitation, the injectable conductor 3 could have multiple strands at one or both ends to stimulate multiple locations simultaneously, or multiple injectable conductors could be injected. Without limitation, some or all of these strands could flare out after placement inside the body to help keep the conductor positioned over a long period of me and during bodily motions. Some treatments require multiple nerves, nerve fibers, or neurons to be stimulated simultaneously. For example, one muscle may require many nerve fibers to be stimulated to achieve full muscle movement. In the brain, often many locations need stimulation to treat a general disorder like anxiety or dementia. In these cases, multiple strands of conductors on a single injectable or multiple injectable conductors could be placed, and one stimulator coil could stimulate all of them or multiple stimulator coils could be used.

Stimulator-Body Configurations

Figure 10:
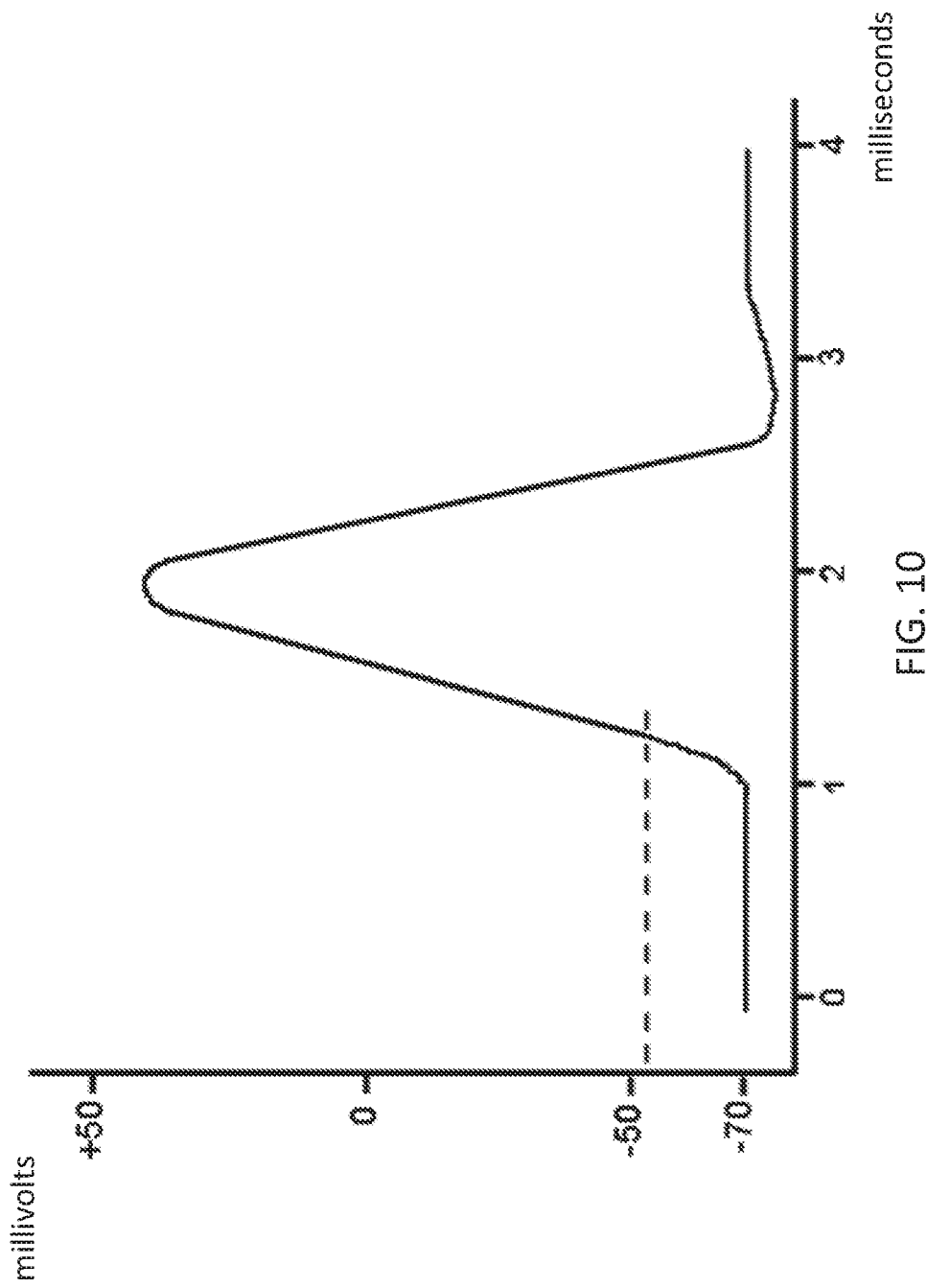
FIG. 10 is an exemplary graph of the pulse shape of an action potential evoked by the stimulator coil of FIG. 8.

FIG. 4a shows how this neural stimulator may be used to excite a peripheral nerve in the human arm. injectable conductor 3 is placed with one end on the nerve to be stimulated. This end should be located on or near the nerve fiber or on or just inside the cell membrane of the axon to be stimulated. The active endpoint of the injectable may be situated just outside the myelin layer of the nerve fiber or penetrate the myelin layer or be located just outside the nerve fiber bundle or penetrate the perineurium layer. The stimulation voltage amplitude at the injectable needs to be around 100 millivolts to stimulate the nerve through the myelin or perineurium layer. If the endpoint of the injectable is touching the nerve fiber or neuron itself, then only about 15 millivolts of amplitude is required at the injectable. See the 15 millivolts difference between the resting potential and the trigger potential of the action potential in FIG. 10, which defines the minimum voltage needed to stimulate.

The other endpoint of the injectable in FIG. 4a and the rest of the injectable conductor should be oriented to avoid nerves and neurons that should not be stimulated, and avoid tissue that could be adversely affected. The orientation should also be such that normal body movements do not cause the active endpoint of the injectable conductor to shift in position over time. For minimal power consumption and maximum stimulation intensity, the long dimension of the injectable should be aligned with the induced electric field from the coil. Based on Faraday's law of induction, the long dimension of the injectable conductor should be parallel to and as close as possible to the windings of the stimulator coil, and away from the center point of the coil.

In general, the closer that the endpoint of the injectable is placed relative to the nerve, nerve fiber, or group of nerve fibers or neurons to be stimulated, the lower the power consumed by the wearable, which can prolong battery life or reduce battery size. In many neural stimulation protocols, an entire nerve or group of nerve fibers must be stimulated in order to achieve the desired result. In a human being, the diameter of some nerves can be up to 5 millimeters. And, some stimulation protocols call for certain nerve fiber bundles in a nerve to be stimulated preferentially relative to other fiber bundles wherein all fiber bundles are located within the same nerve. FIG. 4b show the cross section 40 of an exemplary nerve containing three fiber bundles 41. The nerve itself, each of the fiber bundles, and each of the fibers are wrapped in a sheath that is highly insulating. For this reason, in some methods of using neural stimulator, may involve placement of the injectable conductor inside the nerve, as illustrated in FIG. 4b and have this injectable stimulate the fiber bundle that is closest. Or, two injectables illustrated in FIG. 4c may be placed opposite the nerve cross section and generate an induced voltage on either side of the nerve, and this induced voltage is twice that of the single injectable of FIG. 4b. FIG. 4d shows how multiple conductors could be placed, either with multiple injections or by having multiple strands in one injectable. FIG. 4d also shows how the injectables can be placed off center to preferentially stimulate the fiber bundles in the lower portion of the nerve cross section. In some stimulation sites, the location of the target fiber bundle inside the nerve is not known. In this case, it is desirable to have a set of injectables that can address different bundle locations. FIG. 4e shows such a configuration. Two injectables are placed above and below the nerve, and another two are placed on each side. Here, the rotational orientation of the wearable field generator will determine which of the four injectable endpoints creates the strongest polarization of the axons, allowing for one of several different fiber groups to be preferentially stimulated relative to the other three. FIG. 4f shows the curved injectable, which can hug the nerve and stay in place more effectively, similar to the cuff electrodes that are implanted today. The exposed conductors on each endpoint of the injectable in FIG. 4f create a stimulation across the nerve's diameter. Without limitation, the endpoints of the curved conductor could be off center relative to the nerve to preferentially stimulate a fiber bundle that is also off center in the same direction.

The wearable stimulator 7 is placed on the skin near the injectable conductor 3 in FIG. 4. Without limitation, the wearable portion 7 could be driven by a circuit or microprocessor that senses an upstream neural activity and uses the Neural Stimulator to bridge to the peripheral nerve externally. In this example, these systems could be used as part of another system to bypass nerve pathways damaged by neuropathy, injury, amputation, or another ailment.

Figure 5:
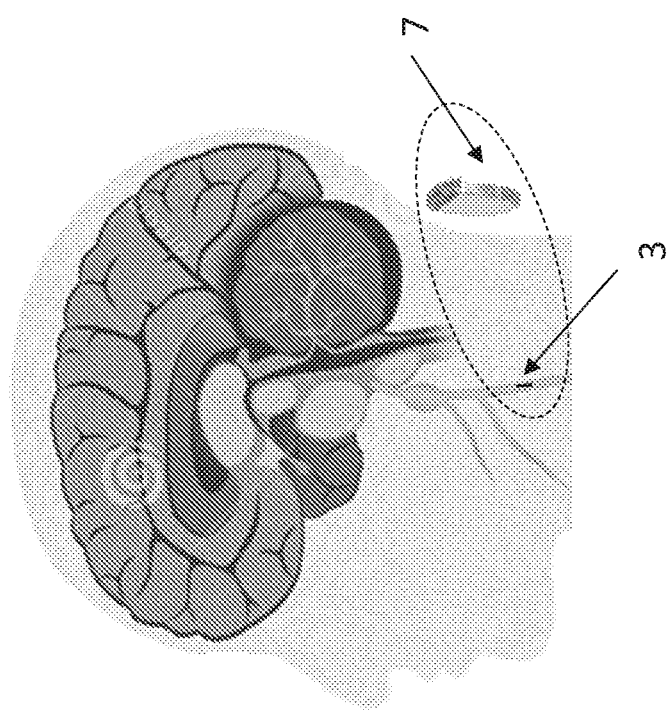
FIG. 5 schematically depicts an injectable conductor with a wearable magnetic field generator, configured for Vagus nerve stimulation.

FIG. 5 shows how this neural stimulator can be used to excite the Vagus nerve. In this case, the injectable conductor 3 is placed with one end on the Vagus nerve or pathway to be stimulated, and the wearable portion 7 is placed close by but outside the body. Without limitation, the Neural Stimulator can help treat epilepsy or other ailment that is alleviated by Vagus nerve stimulation. Known stimulation sites and indications, respectively, are hypoglossal nerve for Obstructive Sleep Apnea, posterior tibial nerve for bladder control, the sensing peripheral or spinal nerve for pain relief, Occipital nerve for migraine, and Vagus nerve for epilepsy.

FIG. 6b shows how an embodiment of the neural stimulator can be used to excite neurons in the deep brain region. In this case, the injectable conductor 3 is placed with one end at the location in the brain where stimulation is desired. The wearable portion 7 is placed close by but outside the head. Without limitation, the neural stimulator can treat Alzheimer's, dementia, anxiety, insomnia, post-traumatic stress disorder, panic attacks, and seizures by placing the injectable conductor in the deep brain such as the hypothalamus, fornix, entorhinal cortex, nucleus basalis or other areas of the brain.

Without limitation, the injectable conductor 3 shown in FIGS. 4, 5, and 6b may be placed with a syringe or other injection system and be guided to the proper location by instantaneous imaging. This imaging could be magnetic resonance imaging (MRI), X-Ray imaging, ultrasound, or other body imaging system.

In these examples and many others, the neural stimulator may greatly reduce the invasiveness of the prior art stimulators, an example of which is illustrated in FIG. 6a. Prior art targeted stimulators require extensive surgery, long wires, large implants, and implanted battery charging or and periodic removal and replacement of the battery. These represent great technical challenges for both doctor and patient, and incur very high costs of implementation.

Driver Circuit for Stimulator Coil

The driver circuit of this neural stimulator manages the applied voltage, current, and power consumption of the stimulating coil effectively to reduce one, two, or all three of these quantities. Relative to the existing magnetic stimulators, various embodiments of the neural stimulator coils described herein may have more turns, which can generate the same magnetic field strength with less current flow. The higher number of turns means that this neural stimulator coil has a higher inductance, or stores more energy. This energy may be stored in the coil as a DC current in between pulses and is reciprocated to and from a parallel capacitor when generating a pulse. Alternatively, the DC current may be gradually erased between pulses, saving even more energy.

The driver circuit's pulse changes current rapidly in the coil creating a rapidly changing magnetic field, thereby creating the large electric field, by Faraday's law, a few centimeters away and inside the body. The voltage generated in the capacitor can be many times greater than the supply voltage required of the circuit. Hence, the driver circuit can use high voltages to achieve a rapid change in current in the stimulating coil, but does not require a high voltage supply. Furthermore, the injectable conductor 3 of the neural stimulator reduces the total magnetic energy required to stimulate action potentials, further reducing the power needed in the external coil. All these mechanisms together render the neural stimulator a far superior apparatus for stimulating electricity in the body than the prior art magnetic stimulators.

Figure 7:
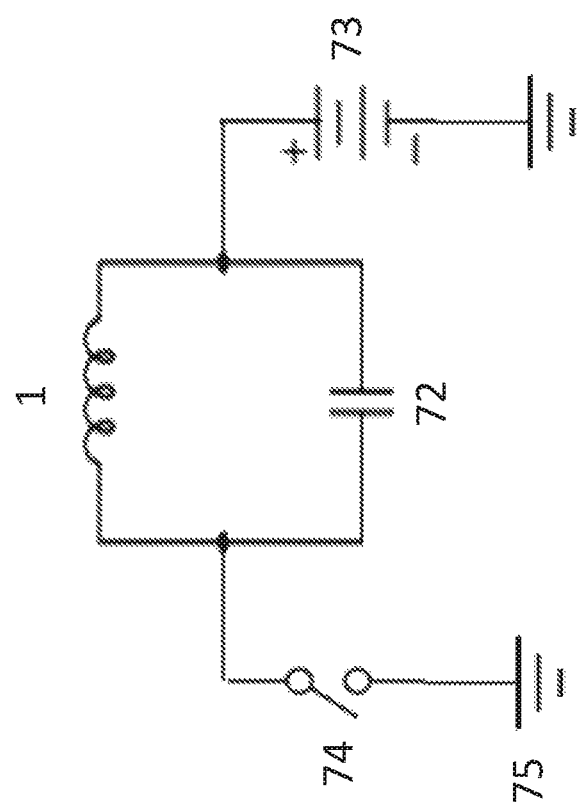
FIG. 7 is a schematic circuit diagram of an embodiment of an electrical driver circuit.

One embodiment of an exemplary driver circuit is depicted in FIG. 7, where the stimulator coil 1 is connected in parallel with a capacitor 72, and this sub-circuit is called a resonant circuit. One side of the resonant circuit is connected to a low voltage power supply 73, The other side is connected through an analog switch 74 to ground 75. The power supply allows current to flow in the stimulator coil when the switch is closed and completes the circuit. The parallel capacitor stores and recycles the high-voltage electrical energy required for the next pulse in the stimulation burst. The switch can additionally turn off power in between bursts to minimize power consumption further.

Figure 8:
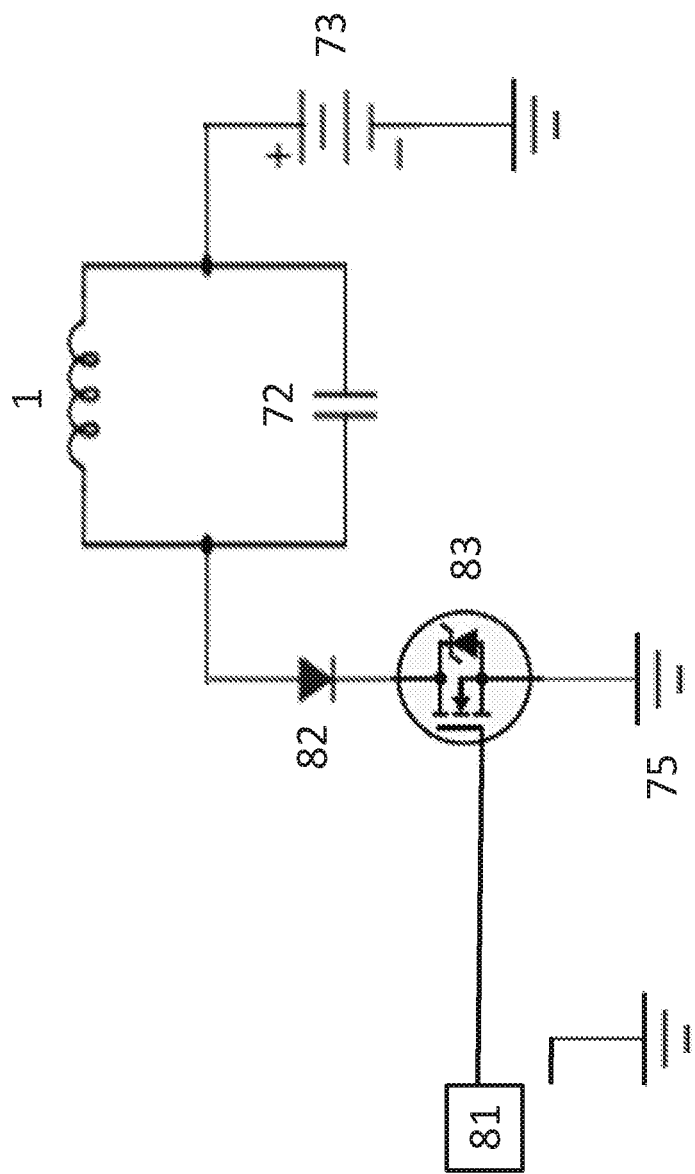
FIG. 8 is a circuit diagram of another embodiment of a driver circuit.

FIG. 8 depicts another embodiment of the drive circuit. Compared to FIG. 7, the switch 74 of FIG. 7 is replaced by a series connection of a rectifier 82 and an N channel MOSFET 83. The pulse generator 81 drives the gate of the MOSFET 83 to turn it on and off. A MOSFET 83 normally functions as an ideal switch, but only when the drain-source voltage is positive. Because the drain-source voltage can sometimes be negative, as will be described later, the rectifier 82 is added in series to prevent the MOSFET 83 from seeing a negative drain-source voltage and preserving characteristics of an ideal analog switch that is open. The pulse generator 81 generates a voltage that turns on and off the MOSFET 83 gate.

Figure 9:
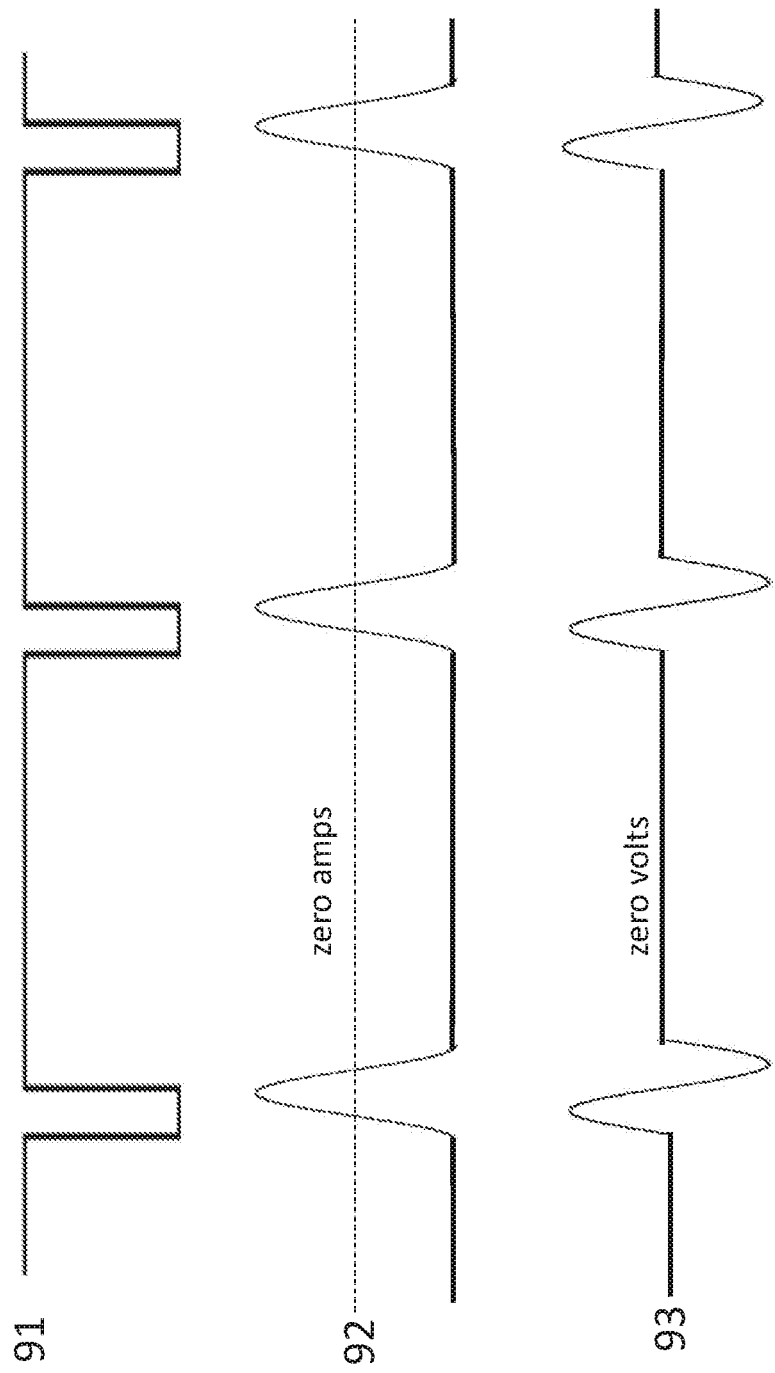
FIG. 9 shows the waveforms of the circuit of FIG. 8 when operating, including the (1) the pulse generator output, (2) the current in the stimulator coil, (3) the magnetic field produced by the stimulator coil which is proportional to the current, (4) the voltage across the stimulator coil, and (5) the electric field induced by Faraday's law a short distance from the coil, which is proportional to the coil voltage.

FIG. 9 shows the waveforms that are generated by the circuit of FIG. 8 when activated by the pulse generator. Most of the time, pulse generator output 91 keeps the gate of MOSFET 83 of FIG. 9 turned "on", but turns it off when a stimulating pulse needs to be created. When the MOSFET 83 of FIG. 8 is turned on for a while, the coil current 92 in FIG. 9 will reach steady state defined by the voltage across the coil divided by its electrical resistance. This steady coil current 92 remains until the pulse generator output 91 drops and thereby the MOSFET 83 gate of FIG. 8 turns off. At this time, the resonant behavior of the stimulating coil 1 and the capacitor 72 of FIG. 8 will begin. In this preferred embodiment, the resonance is aborted after one cycle as the pulse generator output 91 turns the MOSFET 83 gate of FIG. 8 back on. At this time, the steady coil current 92 is restored and the resonance stops.

During the resonant cycle, the coil current 92 follows the shape of one period of a cosine wave. As expected from general circuit theory for an inductor, the coil voltage 93 will follow the derivative of the coil current 92, and hence appears as one period of a sine wave. The period of this sine wave, which is also the width of the biphasic stimulation pulses is equal to SQRT(LC) where L is the inductance of the stimulator coil and C is the capacitance of the parallel capacitor. The inductance of the stimulator coil typically ranges from 0.1 to 20 millihenries, and the capacitance of the parallel capacitor ranges from 0.1 to 10 microfarads. The coil voltage 93 must stay below the rated voltage of available MOSFETs or IGBTs and rectifiers, which is typically 1000-2000 voltage. The system may be configured so that the current pulse 92 amplitude does not exceed the instantaneous current available from a typical wearable battery and supply capacitor, which is typically about 20 amps, but in other embodiments may be in the range of 1 to 10 amps, 10 to 30 amps, or 30 to 100 amps, for example. The RMS average current times the RMS average voltage in FIG. 9 must not exceed the power rating of a wearable power supply, which is 10 to 12 watts for a standard USB battery used to charge smart phones, for example. The power is also limited by the time needed between charging of the wearable battery, which is 50 watt-hours (10 watts for 5 hours) for a one-pound battery using Lithium Polymer chemistry.

Typically, the pulse widths are between 50 microseconds and 1 millisecond, but in other examples could be in the range of 10 to 50 microseconds or 1 to 100 milliseconds, with multiple, preferably biphasic, bursts. Typically, the burst frequencies vary from 10 Hz to 100 Hz, but in other examples could be 1 Hz to 10 Hz or 100 Hz to 1000 Hz. In some embodiments, relatively narrower pulses with higher burst frequencies may be used, while in other embodiments, relatively wider pulses with lower burst frequencies, if the aforementioned ranges are maintained. The ranges of current, pulse width, and burst frequency are also dependent on the degree of stimulation needed. For example, some stimulation protocols just need to regenerate background levels of neural activity while others need to evoke the maximum rate of action potentials of the body. Stimulating muscle movements, for example, require strong stimulations to recruit most or all the muscle fibers to act together as each one is activated by a single nerve fiber. The ranges of current, pulse width, and burst frequency could also be dependent on how close the injectable is placed to the target nerve or nerve fibers or neurons to be stimulated. In some cases, the target nerve group or nerve fiber may be deep within the nerve, and the stimulation from the injectable must traverse one of more fascicles, which shield the stimulation energy, possibly differently for some frequencies versus others. For example, if higher frequencies of stimulation from the injectable are attenuated by the soft tissues in the body, then the wider pulse widths and lower burst frequencies would traverse these tissues with less attenuation than narrower pulse widths and higher burst frequencies. The location of nerve groups within a nerve and nerve fibers within a group are not always the same from one patient to another, and the injectable may need to stay a safe distance away to prevent nerve damage throughout the life the patient. The neural stimulator embodiments described herein can achieve a range of stimulations using the injectable conductor combined with the wearable stimulator. In FIG. 9, the burst rate of stimulation is set by the frequency of the pulse generator output 91. The elapsed time between the start of stimulation pulses to the termination of pulses, or burst width, is set by the pulse width of the pulse generator output 91 (FIG. 9 shows a width of one resonant cycle, but a longer pulse output would create multiple resonant cycles). Finally, the stimulation pulse width is determined by the resonant frequency of the stimulator coil and the parallel capacitor, and this resonant frequency can easily be adjusted by changing the capacitance of the parallel capacitor. Hence, all key parameters of known and desirable wired stimulations systems can be accommodated by the driver circuit design of FIG. 8.

The magnetic field created by a coil is proportional to the current flowing within the coil. Hence, the coil current 92 waveform in FIG. 9 also represents magnetic field 92 emanating from the coil and penetrating the body.

Similarly, Faraday's law states that the induced electric field in space of an electromagnetic wave is proportional to the derivative of the magnetic field. For this reason, the coil voltage 93 waveform in FIG. 9 also represents the electric field 93 emanating from the coil and penetrating the body. It is this electric field that evokes or depolarizes the action potentials normally appearing the body or the brain, at the location of the injectable conductor.

The electric field created by the neural stimulator embodiments described herein and shown in the Electric Field 93 of FIG. 9 can be oriented to further evoke the natural action potentials already existing in the body, or could depolarize them by reversing the leads on the simulating coil 1 of FIG. 8.

One way to reduce the amplitude of the undershoot in coil voltage 93 of FIG. 9 is to add some ferromagnetic metal around the coil opposite the side facing the body. The presence of the metal will create eddy currents, which will turn into heat. These losses will make the resonance die out faster, and hence make the undershoot have smaller amplitude than the initial pulse. Another way to reduce the amplitude is to add a resistor in series or in parallel with the stimulator coil 1. The resistor heat has the same effect as the eddy currents, hence reducing the amplitude of the undershoot relative to the main pulse.

Figure 11:
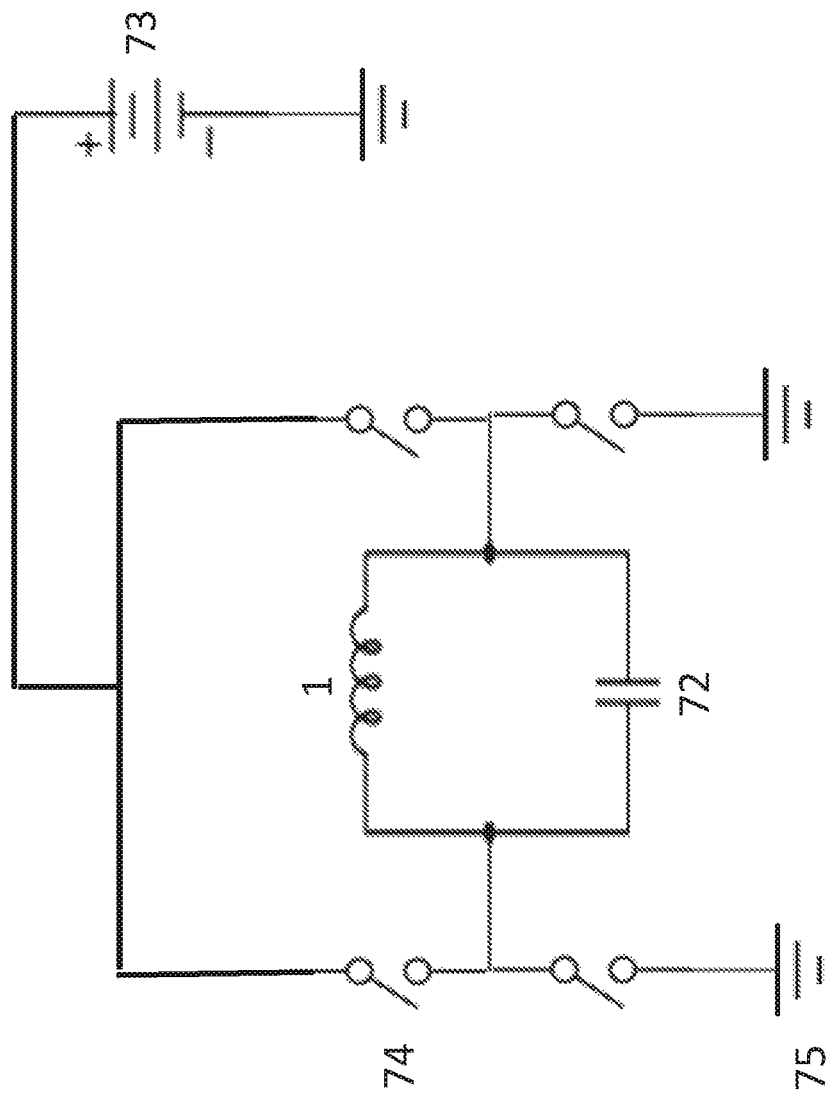
FIG. 11 shows a circuit diagram of another exemplary electrical circuit that provides for separation of the positive and negative pulses in time.

FIG. 11 shows yet another embodiment of a neural stimulator system. The resonant combination of the stimulating coil 1 and parallel capacitor 72 is now driven bi-directionally by an H-driver. The H driver has four analog Switches 74, and the resonant circuit is situated in the center of the H. Power is supplied through one of two switches to the two upper legs of the H, and ground is connected through one of two switches to the two lower legs. Two switches, upper left and lower right are turned on to flow current into this resonant circuit on one direction, and the other two switches, upper right and lower left are turned on to flow current in the opposite direction. This circuit can separate, in time, the electric field 93 cosine wave pulse of FIG. 9 into two pulses, one positive and one negative. The waveforms for this approach will be described later below.

Figure 12:
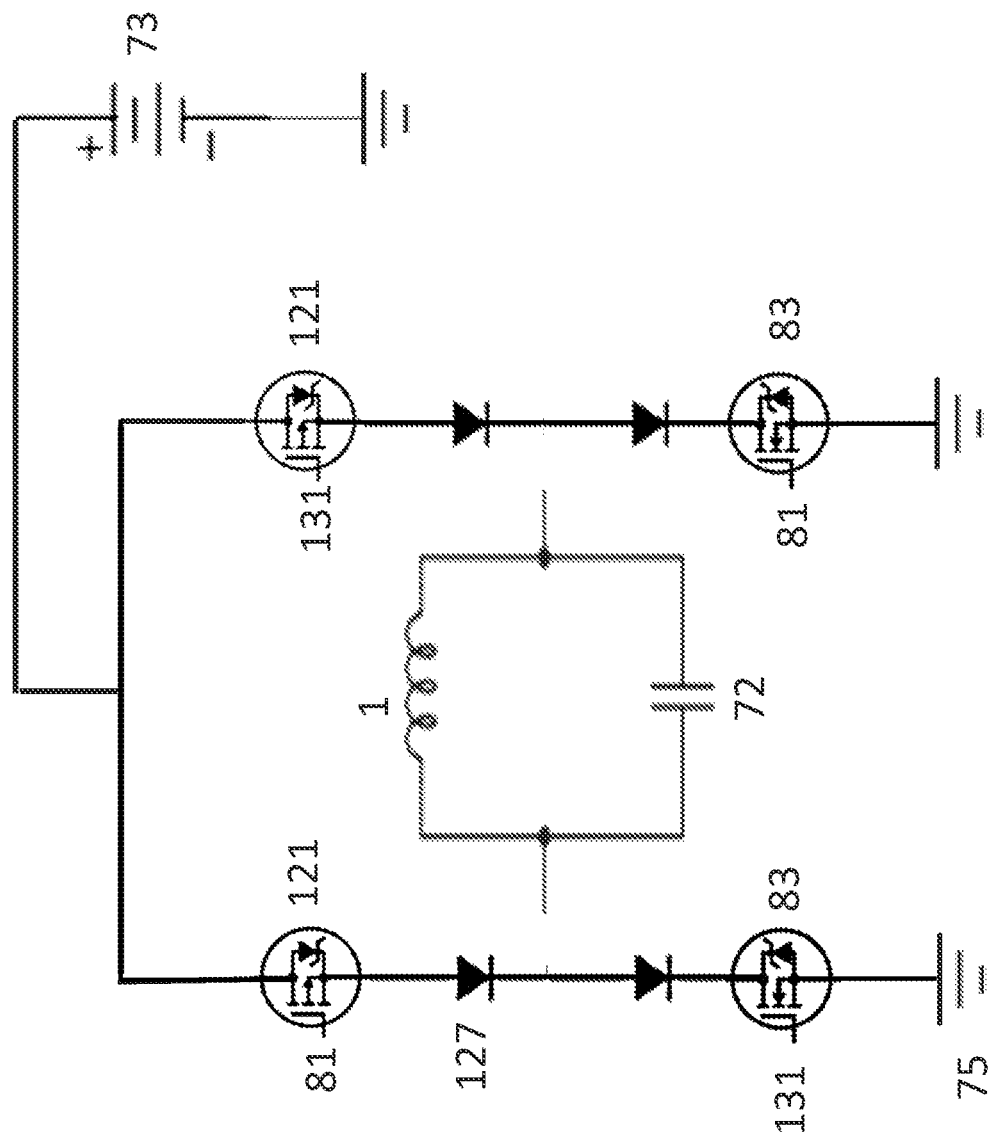
FIG. 12 depicts another embodiment of a driver circuit of the ideal circuit depicted in FIG. 11.

FIG. 12 shows the circuit of FIG. 11, but with each of the upper analog switches described for FIG. 11 replaced by a series connection of p-channel MOSFETs 121 and rectifiers 127 and the lower analog switches replaced with a series connection of n-channel MOSFETs 83 and rectifiers 127. This H-driver circuit with these components is in a standard H-driver configuration used for other reversible drive systems like DC motors. As in FIG. 8, the rectifier 127 is added to allow the MOSFETs 83 and 121 to behave like an ideal analog switch regardless of the polarity of voltage. Also, the MOSFET 121 is a P channel MOSFET to facilitate switching current from the power supply instead of to the ground, for which the N channel MOSFET is designed. The pulse generator output 131 drives the gates of one pair of MOSFETs 83 and 121, and the inverse of the pulse generator output 131 drives the gates of the other pair. In this case, the MOSFETS 83 and 121 pairs are always driving current in one direction or the other.

Figure 13:
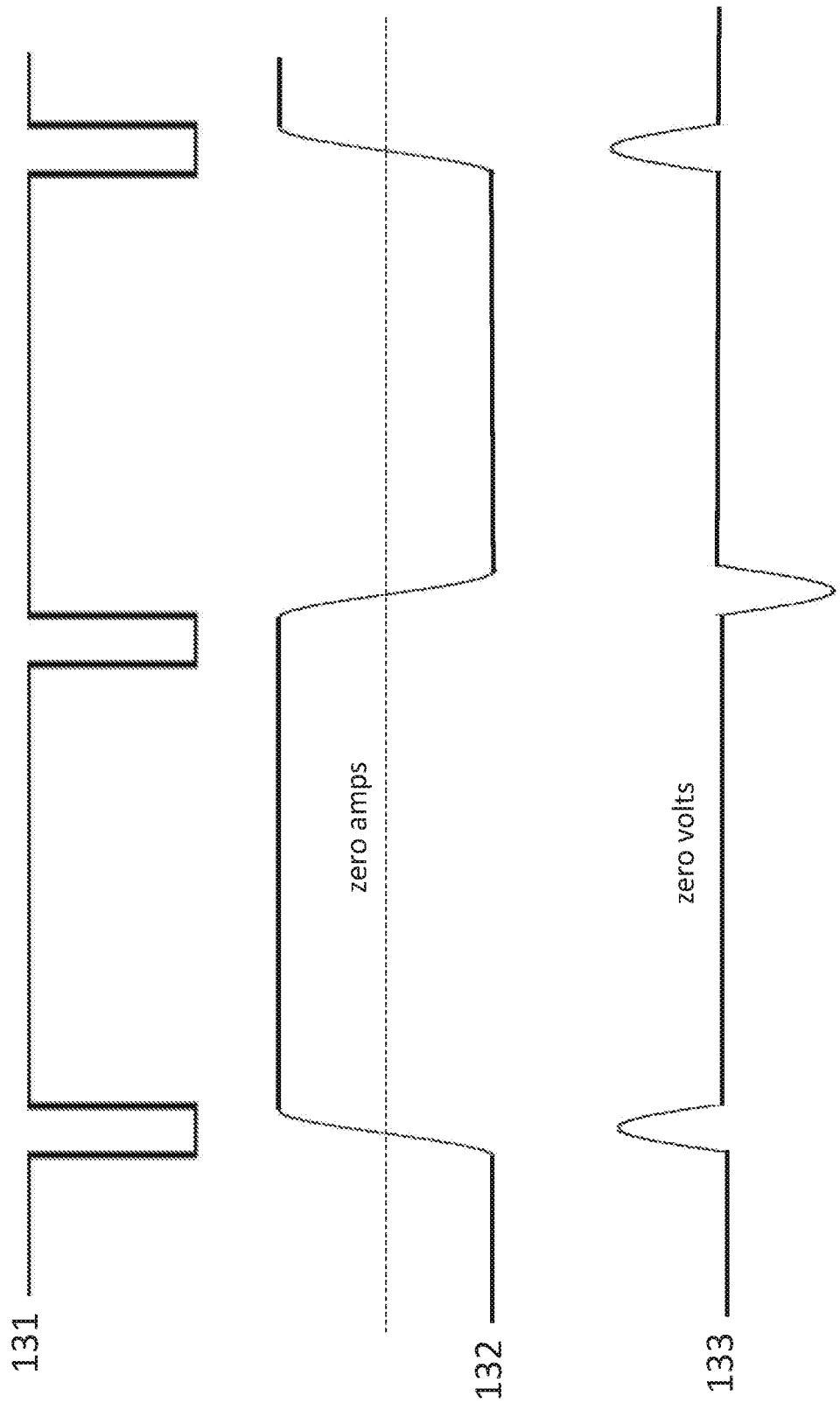
FIG. 13 shows the waveforms of the circuit of FIG. 11 when operating, including the following: (1) the pulse generator output, (2) the current in the stimulator coil, (3) the magnetic field produced by the stimulator coil which is proportional to the current, (4) the voltage across the stimulator coil, and (5) the electric field induced by Faraday's law a short distance from the coil, which is proportional to the coil voltage.

FIG. 13 shows the waveforms of the coil current 132 and coil voltage 133 for the circuit of FIG. 12 when activated by the pulse generator output 131. This embodiment allows for the stimulating coil 1 to have, while all switches are open and resonance is allowed to occur between the stimulator coil and the parallel capacitor, the half-cosine positive and half-cosine negative pulses separated in time. A positive electric field 133 half-cosine pulse is created in the body when the stimulating coil 71 experiences a positive current transition, and a half-cosine negative pulse is created on a negative current transition. In biphasic stimulation, the desire is to avoid buildup of charge in the body. This can be accomplished by having pulses of the opposite polarity occur after the leading pulse. The circuit of FIG. 12 and its waveforms in FIG. 13 allow for the charge from the leading pulse to be removed later in time. The time between these pulses of opposite polarity allows for an additional degree of freedom in the stimulation protocol. For example, this separation of the positive from negative pulses might allow for the amplitude of the pulses to be less since the negative pulse can be delayed until the refractory period of the action potential. During the refractory period, the negative pulse does not negate some of the effects of the leading pulse, but still prevents charge build-up.

Without limitation, the rectifier in FIGS. 8 and 12 may each be multiple rectifiers ganged together in series or in parallel or both to distribute the current and voltage and stay below the rated voltage and/or rated current of each individual rectifier. Also without limitation, the MOSFETs of FIGS. 8 and 12 may each have multiple MOSFETs connected in parallel or series for the same purpose. In addition, these MOSFETs could be replaced by Insulated Gate Bipolar Transistors (IGBTs), Darlington transistors, or bipolar transistors, without limitation. Also without limitation, the output of the pulse generator may originate from a microprocessor-based controller or computer and have multiple transistor driver stages to adequately turn on and off the MOSFETs or other driver transistors. Again, without limitation, multiple instances of this driver circuit could be used to drive multiple coils synchronously for the electric fields of the multiple coils to add together in a focused region, or subtract to remove stimulation where it is not wanted, or any combination of these. The double coil used by Brainsway (Jerusalem, Israel) is an example of where two coils are used to better focus the magnetic field inside the brain and improve the resolution of treatment for magnetic stimulation.

Driver Circuit Design

The circuit illustrated in FIG. 8 was built wherein the stimulator coil 1 was an air-core coil of approximately 500 turns of 18 AWG (American Wire Gauge) copper magnet wire, wrapped on a spool of 2.0 centimeter inner diameter, 5.0 centimeters outer diameter, and 4 centimeters thickness. The capacitor 72 was 0.5 microfarads rated at 2000 volts, and is available from Digikey as part number 338-4169-ND. The rectifier 82 was rated at 1000 volts and 3 amps, and was available from Digikey as part number 1N5408-E3/54GICT-ND. The N channel MOSFET was implemented as four MOSFETs ganged together in parallel and each one was rated at 1200 volts. The MOSFETs are available from Digikey as part number 1242-1164-ND. The power supply 73 was variable up to 30 volts DC and 10 amps. The pulse generator 81 is available from BK Precision as part number 4030.

Figure 14:
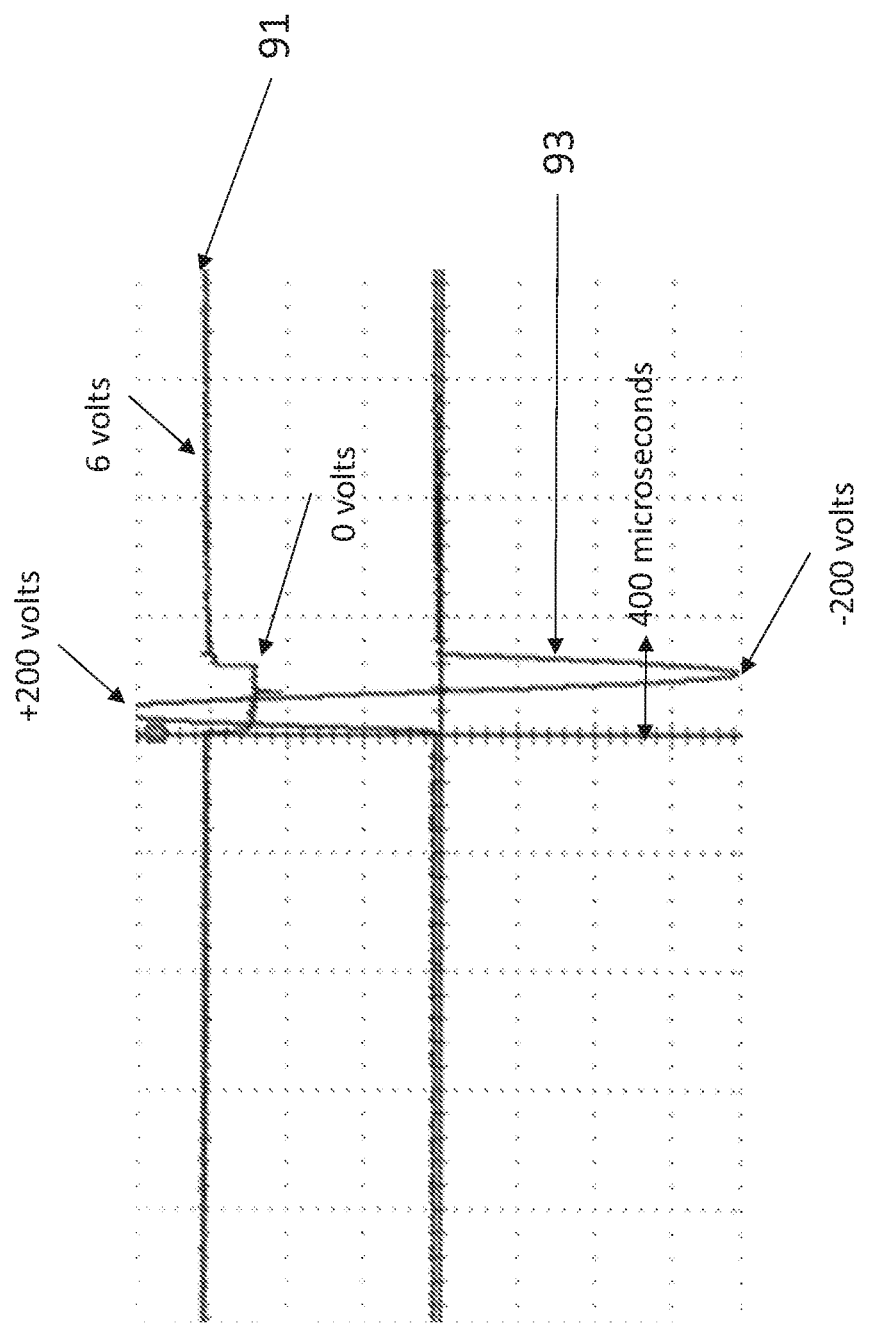
FIG. 14 shows an oscilloscope trace of the coil voltage of the driver circuit of FIG. 8 built and combined with an exemplary stimulator coil.

FIG. 14 shows the oscilloscope waveforms of this preferred embodiment of FIG. 8 using the parts described. The pulse generator output 91 (upper trace) is at 8 volts most of the time, which turns on the MOSFET and for 400 microsecond bursts is 0 volts which turns off the MOSFET and lets the stimulator coil and parallel capacitor resonate for one cycle. Here, the resonance period is 400 microseconds. The stimulator coil Voltage 93 (lower trace) has an amplitude of 200 volts. These waveforms match those predicted by FIG. 9. Note also that the voltage rises to its maximum in less than 100 microseconds, and this was accomplished with 10 volts DC as the power supply. Hence, it is shown that the coil voltage of 200 volts can be much greater than the supply voltage of 10 volts. The pulse generator 81 had a repetition rate of 100 cycles per second (not evident in FIG. 14).

Figure 15:
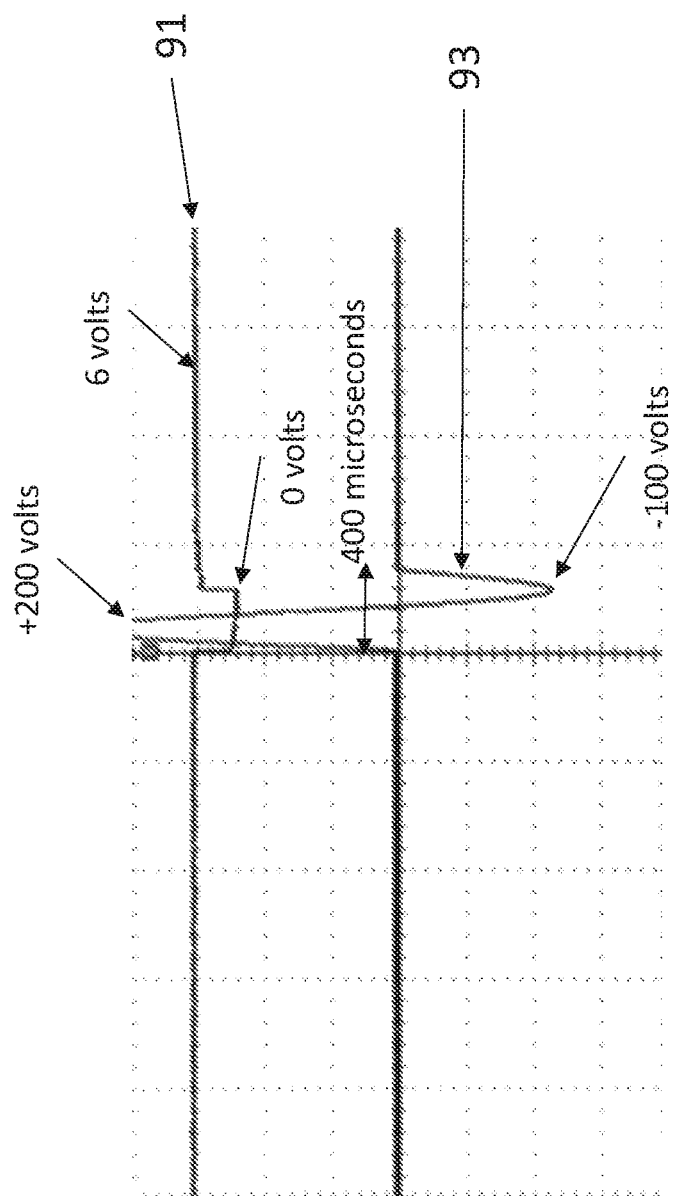
FIG. 15 shows an oscilloscope trace of the coil voltage of the driver circuit of FIG. 8, with the addition of a metallic and ferromagnetic core into the coil.

FIG. 15 shows the oscilloscope waveforms of this preferred embodiment of FIG. 8 using the parts described, but adding a ferromagnetic metal (steel) on the back of the stimulator coil 71. Without limitation, this metal could also have been iron, cobalt, nickel, or any alloy of these with each other or with other metals. Here, the amplitude of the undershoot pulse is now less than half that of the positive sinusoidal pulse. This characteristic of a smaller amplitude of undershoot relative to the main pulse creates an asymmetric pulse for those stimulation protocols that specify this shape.

Pulse Shapes

Figure 16:
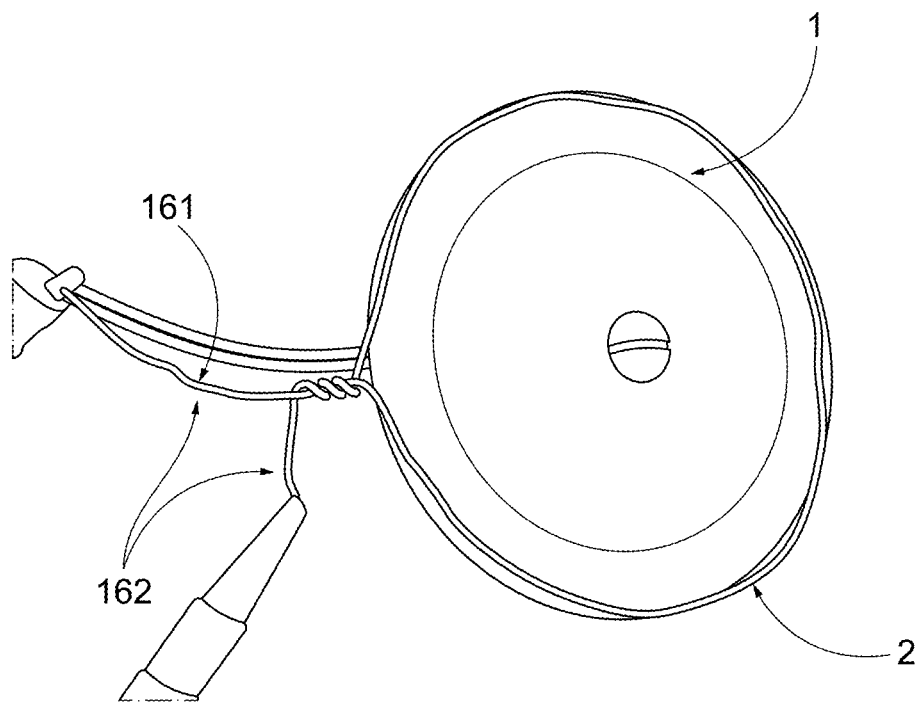
FIG. 16 is an exemplary embodiment of a stimulator coil with windings located in the periphery of the plastic spool, with a single-turn induction coil to pick up the induced voltage from the coil when activated.

FIG. 16 shows another exemplary simulator coil 1 that is 3.5 inches in diameter with the windings in the outer 0.5 inch periphery, with lead wires 161. A single-turn induction coil 2 was used to measure the induced voltage produced by the stimulator coil 1. A driver circuit like the one illustrated in FIG. 8 was connected to stimulator coil 1, including a 0.0047 microfarad parallel capacitor. The white disk is the flange for the top side of the coil's spool. The back perimeter is black tape to hold the windings inside the outer portion of the spool. The screw in the middle reinforces the two flanges of the spool.

Figure 17:
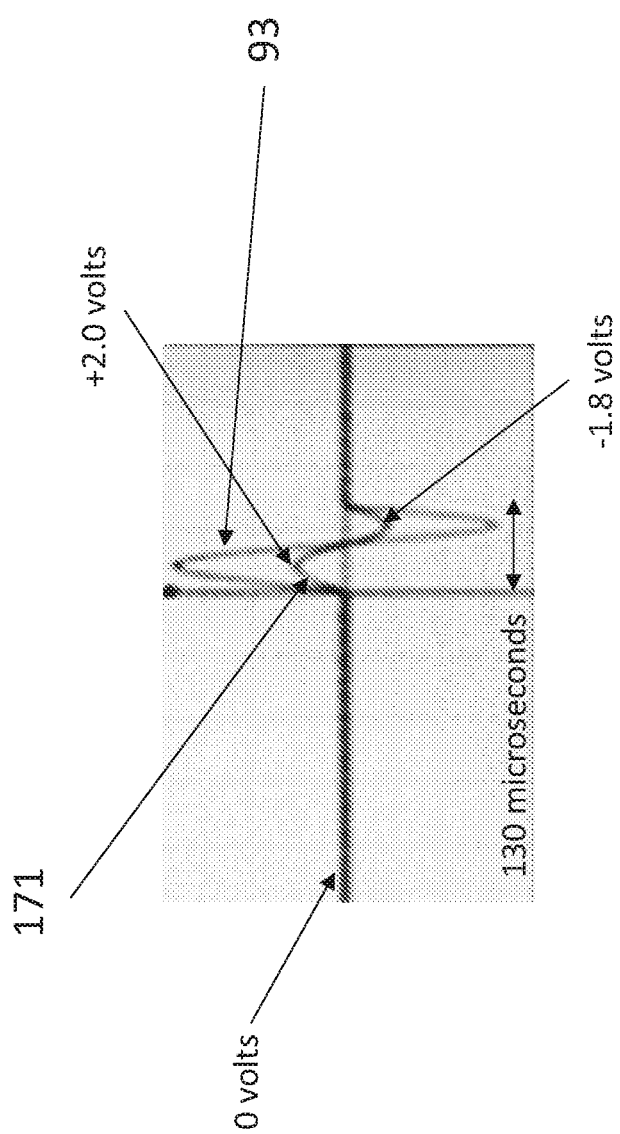
FIG. 17 are the oscilloscope traces of the voltages in the stimulation coil and the induction coil when activated by the circuit of FIG. 8 when the pulse width of the pulse generator is widened to allow for one resonant cycle.

FIG. 17 shows the stimulator coil voltage 93 on an oscilloscope along with the single-turn induction coil voltage 171. Both signals have a period of 130 microseconds on the horizontal time axis. The peak to peak voltage induced in a full turn 171 was about 2.0 volts, such that 20 millivolts would be expected in a 3 mm injectable conductor, as the ratio of the injectable length to the induction coil length is 1/100. The 20 millivolts excitation across electrodes spaced by 3 mm is known to be strong enough to evoke action potentials (the difference between the resting potential of −70 millivolts and the trigger potential −55 millivolts is 15 millivolts in FIG. 10) if no myelin exists between the endpoint and the neuron, so this stimulator coil 1 in FIG. 16 and associated driver circuit is promising for a laboratory demonstration. Note that the stimulation amplitude could be increased by increasing the length of the injectable conductor proportionately or by increasing the supply voltage proportionately. In mammals and human beings, the range of stimulation voltages required at the injectable is between 10 and 20 millivolts if no myelin layer is intervening.

Figure 18B:
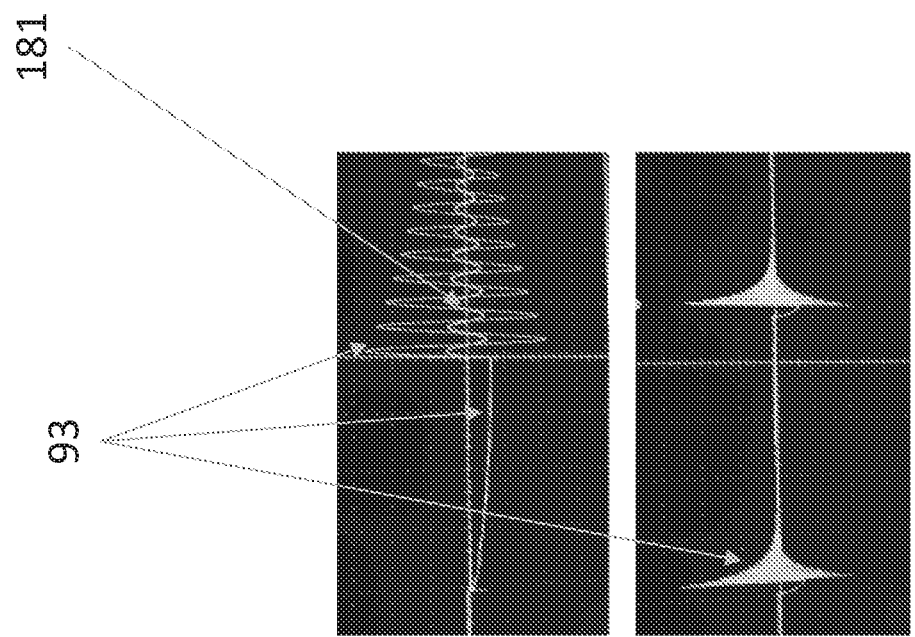
FIG. 18a and FIG. 18b show the induced voltage when the pulse width of the pulse generator in FIG. 8 is widened to allow for two or more resonant cycles.
Figure 18A:
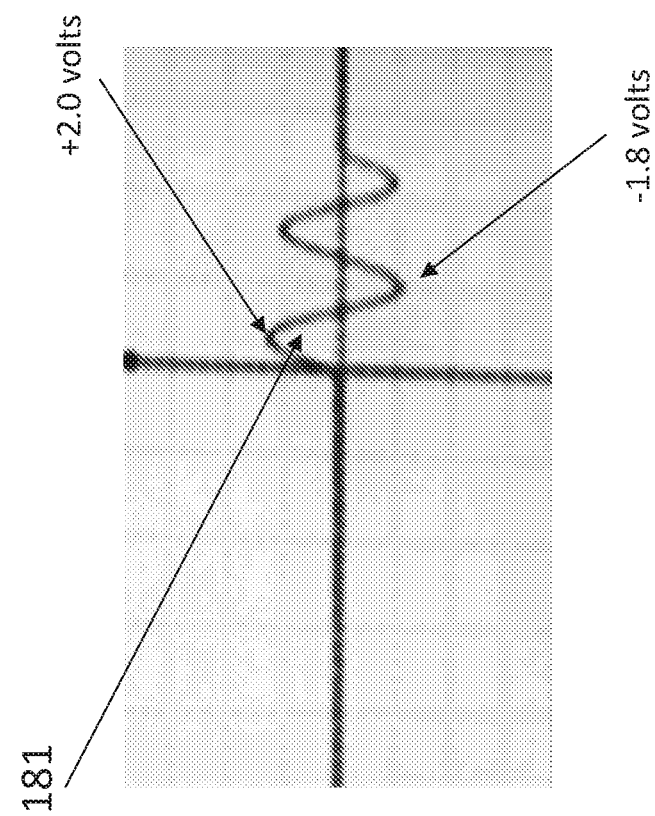

FIG. 18a shows that by doubling the pulse width from the pulse generator, two cycles of the resonance can be achieved for stimulation protocols that benefit from these pulse shapes. In FIG. 18a, oscilloscope trace 181 is the induced voltage in the single-turn Induction coil and has similar amplitude as that of the single cycle pulses of FIG. 17. The time duration of the two-cycle resonant pulse pair is 260 microseconds.

FIG. 18b shows that the pulse width from the pulse generator can be lengthened such that the circuit of FIG. 8 is turned off except when a burst of decaying resonant pulses is needed for stimulation. Trace 93 is the voltage across the stimulator coil 1 in FIG. 8 and its maximum amplitude is 280 volts and the period of the resonance is 200 microseconds. The pulse generator 81 in FIG. 8 is off until Trace 93 starts to become negative from the center axis. After turn on, the voltage is applied to the stimulator coil 1 of FIG. 8 slowly approaches the supply voltage. Trace 181 in FIG. 18*b* is the induced voltage in a single-turn induction coil, and its maximum peak-to-peak voltage is 1.2 volts. In FIG. 18*b*, the pulse generator turns on the circuit of FIG. 8 for a time to allow the steady-state current to build up in the stimulator coil. Once this steady state is reached, the pulse generator turns off the circuit of FIG. 8, and the stimulator coil and capacitor are free to resonate, generating a decaying series of sinusoidal cycles of trace 93. The lower portion of FIG. 18*b* shows the bursts of decaying sinusoidal pulses, and the burst rate is 20 bursts per second, or 20 Hz.

The stimulation protocol of FIG. 18*b* saves energy by not flowing current in the stimulator coil between bursts. The pulse generator 81 of FIG. 8 turns off the stimulator coil except for the 2-millisecond time duration of the build-up of stimulator coil current prior to the resonant burst. After being turned on for 2 milliseconds, the pulse generator keeps the stimulator coil off for 48 milliseconds before repeating the cycle. Hence, the power supply 73 is FIG. 8 is only being tapped 5 percent of the time.

Figure 19:
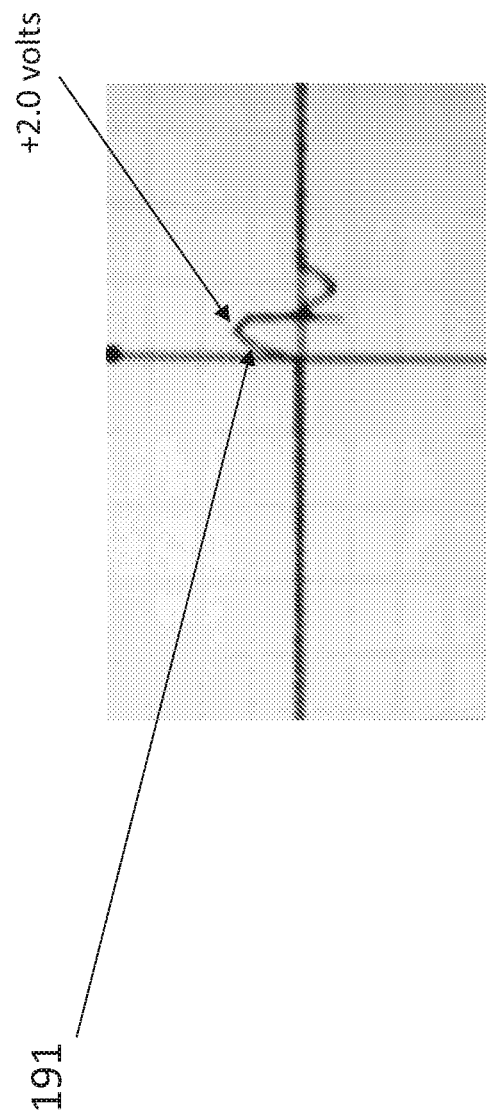
FIG. 19 shows the induced voltage when the pulse width of the pulse generator is shortened to allow for only a partial resonant cycle of circuit of FIG. 8, creating a symmetric stimulation signal.
Figure 20:
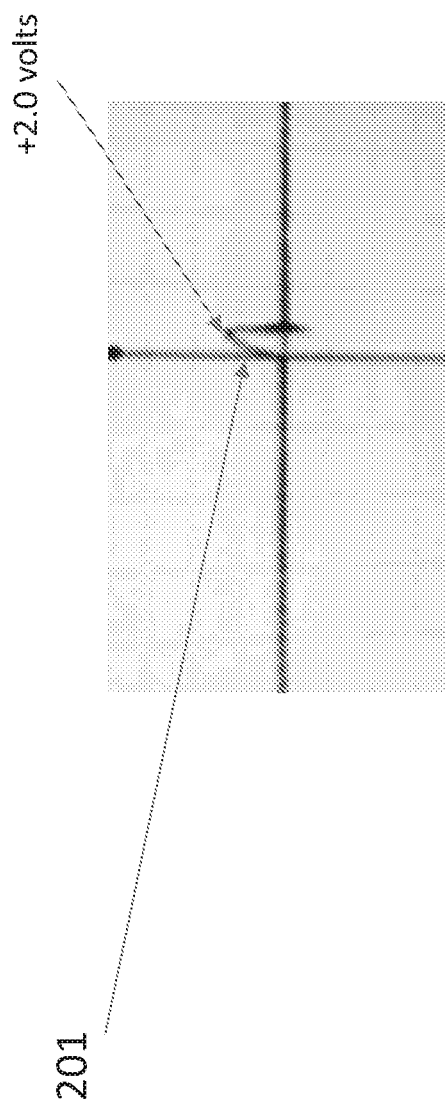
FIG. 20 shows the induced voltage when the pulse width of the pulse generator is shortened further to allow for only the positive portion of a resonant cycle of circuit of FIG. 8, for stimulation protocols that required only one polarity of charge.

FIGS. 19 and 20 show how asymmetric pulse shapes may be generated just by reducing the pulse width of the pulse generator 81 in FIG. 8. In FIGS. 19 and 20, the same hardware was used as in FIGS. 17 and 18*a* and the single-turn induction coil voltage amplitude of Traces 191 and 201 was again 2 volts peak to peak and the period was 130 microseconds. FIG. 19 shows that an asymmetric pulse shape, wherein the positive portion of a single sinusoidal period is greater than the negative portion, is achieved when the pulse generator pulse 81 of FIG. 8 width is narrowed to less than one resonant cycle, as illustrated by the single-turn induced coil voltage 191. FIG. 20 shows how a positive-only pulse, wherein the pulse is a positive portion of a sinusoid that is terminated by turning off the switch before it naturally reaches zero, is achievable by further narrowing the pulse width of the pulse generator. Without limitation, these pulse shapes are available from the driver circuit when they are desired for the stimulation protocol.

Wearable Coil Designs

FIGS. 21-22 depicted various exemplary configurations of the wearable coil devices that may be used, generally characterized by flattened coil shapes that are more appropriate to be worn against the skin or on the outside of the body. The flattened coil shapes may permit the user to continue to ambulate and/or his or her daily activities without protruding from substantially from the body, or from underneath the user's clothing. In some variations, the flattened shape of the wearable coil device or its housing may have a height relative to the skin surface that is significantly less than the width and length of the device. In some variations, the absolute height of the wearable coil device is less than 4 cm, 3 cm, 2 cm or 1 cm, for example.

Figures 21A, 21B:
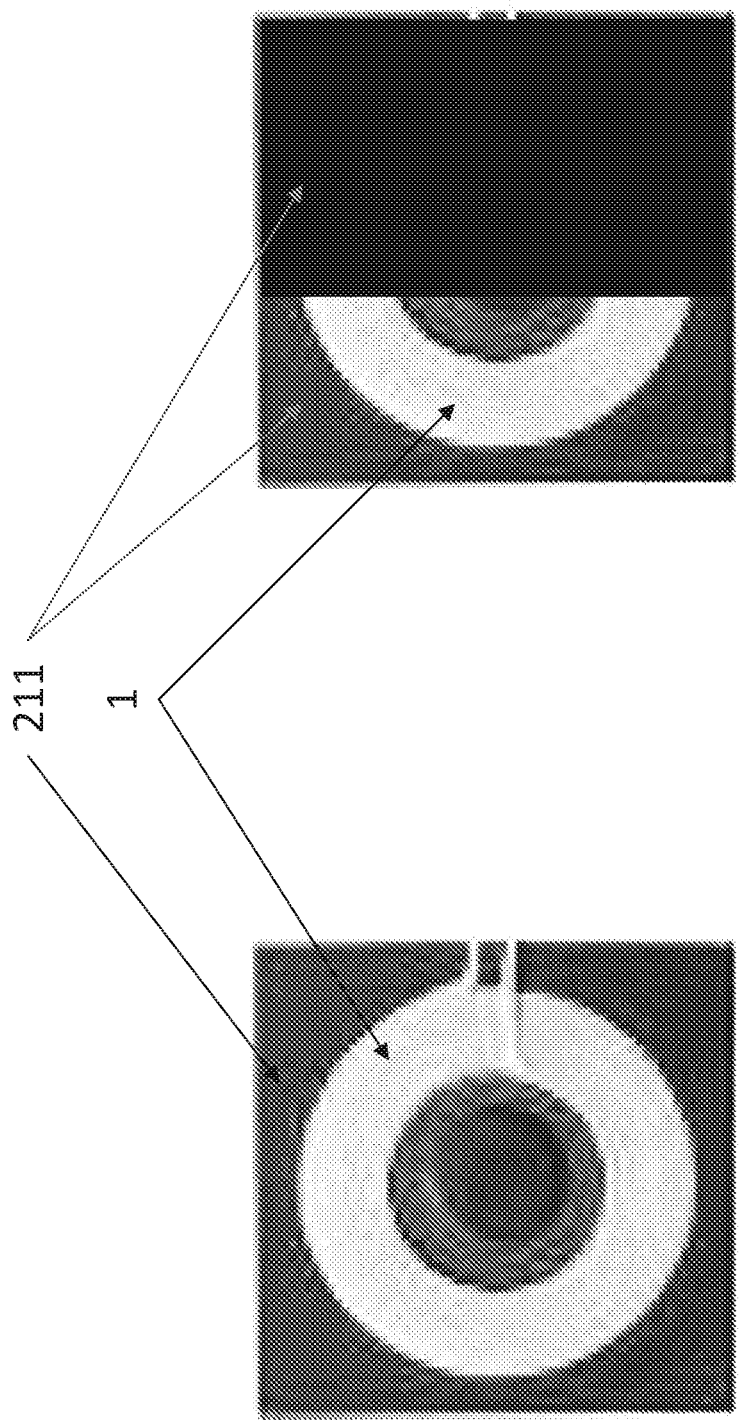
FIGS. 21a and 21b show the placement of high-permeability material on the first and second opposing faces, respectively, of a planar, spiral stimulator coil.

FIGS. 21*a* and 21*b* show a flat coil that could be made from either a rigid or flexible circuit board. The diameter of the coil and hence the width of the circuit board should have the same relationship of 4× the needed penetration depth, or a circuit board width and height of between 1 cm and 40 cm. The rigid material could be the industry standard FR4, or could be glass, or hard plastic with a thickness between 0.5 mm and 2.0 mm, with the smaller thickness for smaller diameter coils and the larger thickness for larger coils. The flexible material could be the industry standard polyimide, or could be BoPET, polyethylene, polyurethane, nylon or PTFE, The material is selected to achieve the flexibility to follow the contour of the skin, but strong enough to be durable after multiple applications of the stimulator. The thickness of the flexible material is between 12.5 and 200 microns, again depending on the diameter of the coil that is supported.

In these designs, the windings of the coil on one side are facing the body, and the injectable is parallel to the windings and as close as possible to the windings. This portion of the windings facing the injectable conductor produce a fringing magnetic field that reaches into the body. These fringing magnetic fields can be made stronger if the magnetic field from the rest of the coil is contained by a material with high magnetic permeability. If this material is not electrically conductive, then it will not lose power from eddy currents within the material. Iron and steel are examples of high-permeability materials that are electrically conductive. Ferrite, in either flexible or rigid form is an example of a high-permeability material that is not electrically conductive, and hence a preferred material. High permeability materials, both conducting and non-conducting, generally have a magnetic permeability that is 10 to 1000 times higher than that of air, but any material with relative permeability greater than 1 would have a desired effect. The thickness of the high permeability material should be between 1 mm and 2 cm depending on a variety of factors including the material's permeability, the weight added to the wearable device, and the width and height of the coil.

FIG. 21*a* shows how a flat high-permeability material 211 can be added to the back of the coil 1, the side not facing the body, to increase the magnetic field strength and hence provide higher stimulation at the injectable. Adding this material 211 can also reduce the power consumption of the wearable needed for stimulation, especially if it is not electrically conductive.

Figure 22B:
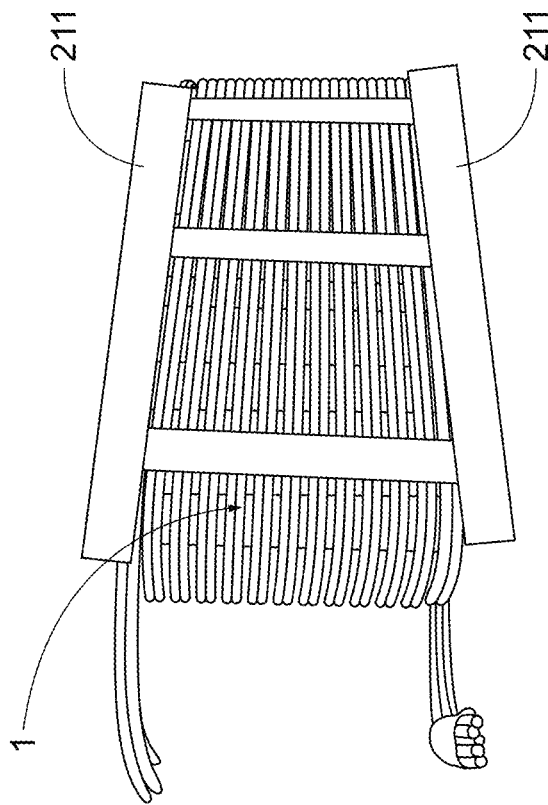
FIGS. 22a and 22b are perspective view of an exemplary flattened oval stimulator coil with and without high permeability materials, respectively.
Figure 22A:
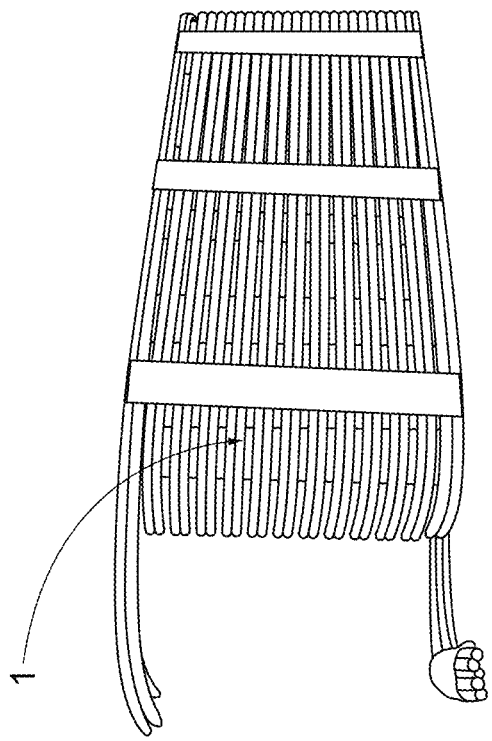

FIG. 21*b* shows how this material 211 can also cover body-facing side of the return windings 1 whose adjacent magnetic field is not used for stimulation, further increasing the coil's efficiency. FIGS. 22*a* and 22*b* show another coil 1 configuration that is flattened into a cylindrical shape with an oval cross-section. Here, the windings on one long side of the oval faces the body and the injectable conductor, and the return windings are on the other long side of the oval, away from the body. The configuration of FIG. 22*b* similarly uses the high permeability material 211 between the body-facing windings and the return windings. The width and height of the windings should be approximately equal to the penetration depth to optimize power consumption, hence between 0.25 cm and 10 cm. Because this coil is elongated vs. the round shape of other coils discussed here, it's form factor is more suitable for some parts of the body like the arms, legs, and extremities.

Animal Study

Figure 24:
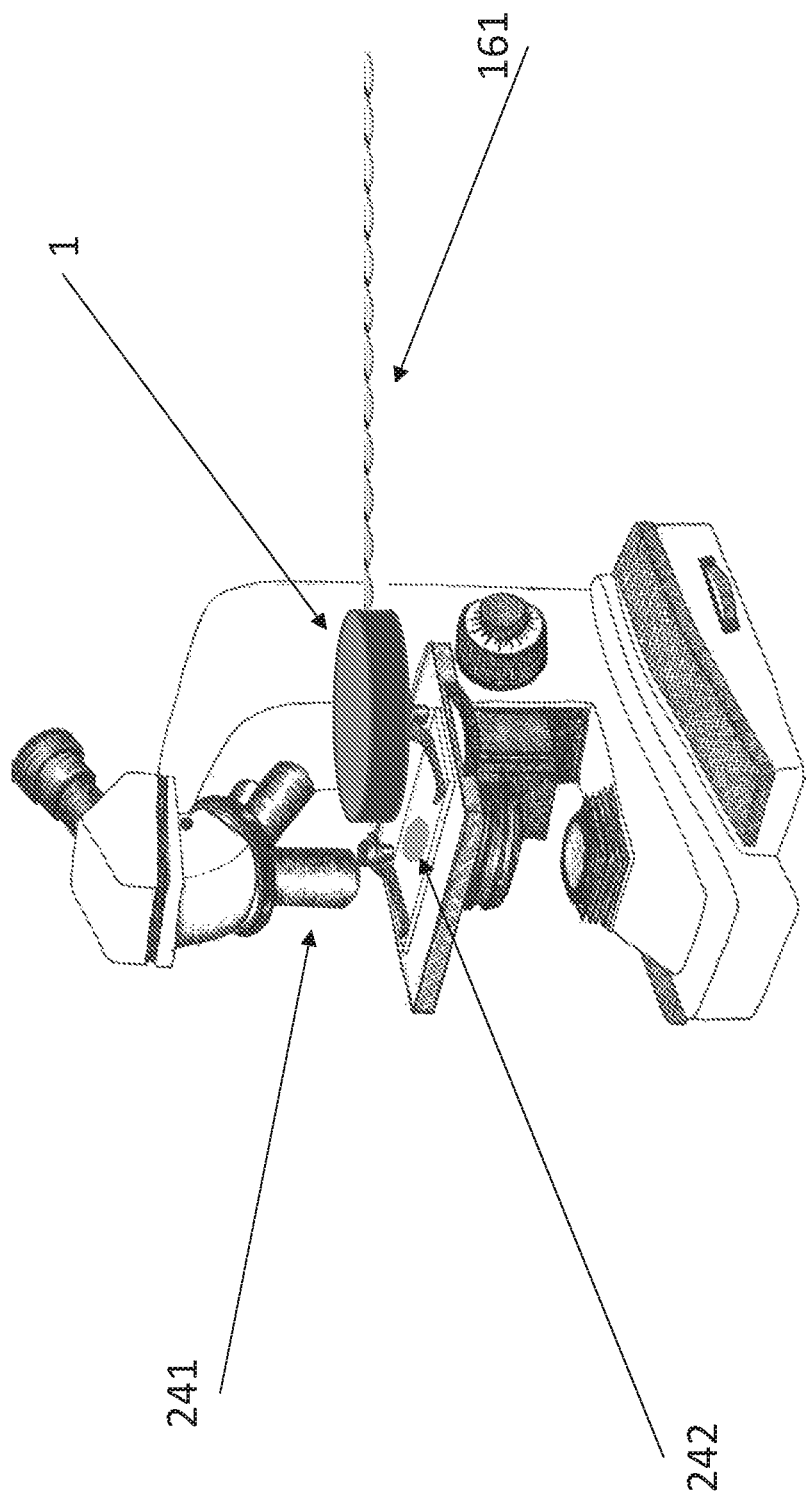
FIG. 24 shows the microscope and electrophysiological system of an experiment to stimulate action potentials in a live brain slice taken from a mouse under a microscope.

FIG. 24 shows an apparatus that was used to prove that this Neural Stimulator can stimulate live tissue and cause action potentials to occur. A mouse brain slice sample 242 was placed under a microscope with objective lens 241 and the experiment was performed while this brain slice was still alive and active. The stimulator coil 1 was placed 3 centimeters from the brain slice with the windings parallel to the brain slice. Lead wires 161 are connected to the same driver circuit used in FIGS. 16-17 Stimulator coil 1 was 7.5 cm in diameter and 1.25 cm thick, and weighed 0.25 pounds, wherein most of the weight was in the copper magnet wire used for the coil windings.

Figure 25:
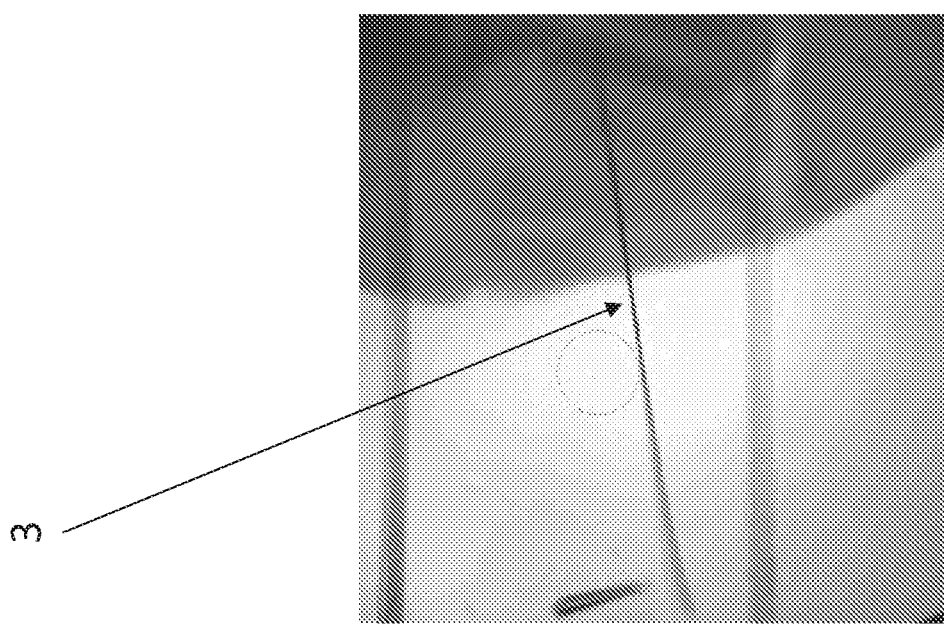
FIG. 25 is a microscope image of an injectable conductor placed in a brain slice.

An injectable conductor 3 made of uninsulated nichrome with diameter 17 microns and length 3 mm was placed in the brain slice, as illustrated in the microscope image of FIG. 25. The magnification of the microscope image of FIG. 25 was 10×.

Figure 26:
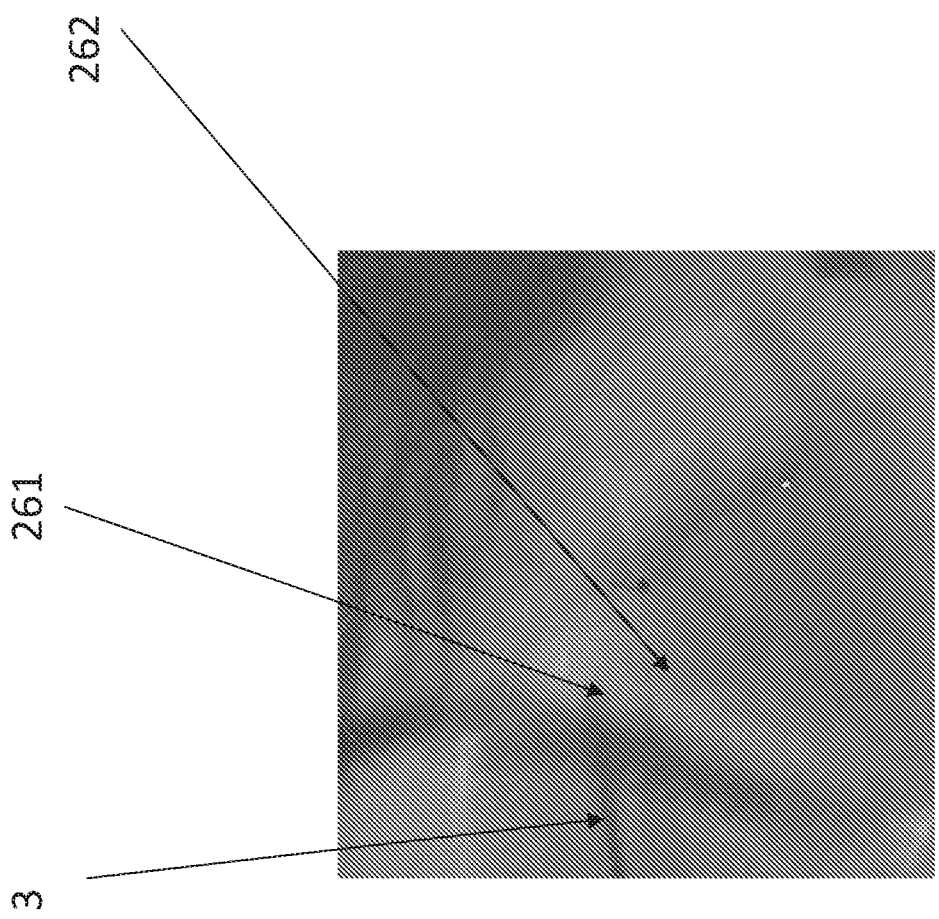
FIG. 26 is a microscope image of the tip of the injectable conductor and a sensor placed on a nearby neuron to detect action potentials.
Figure 27:
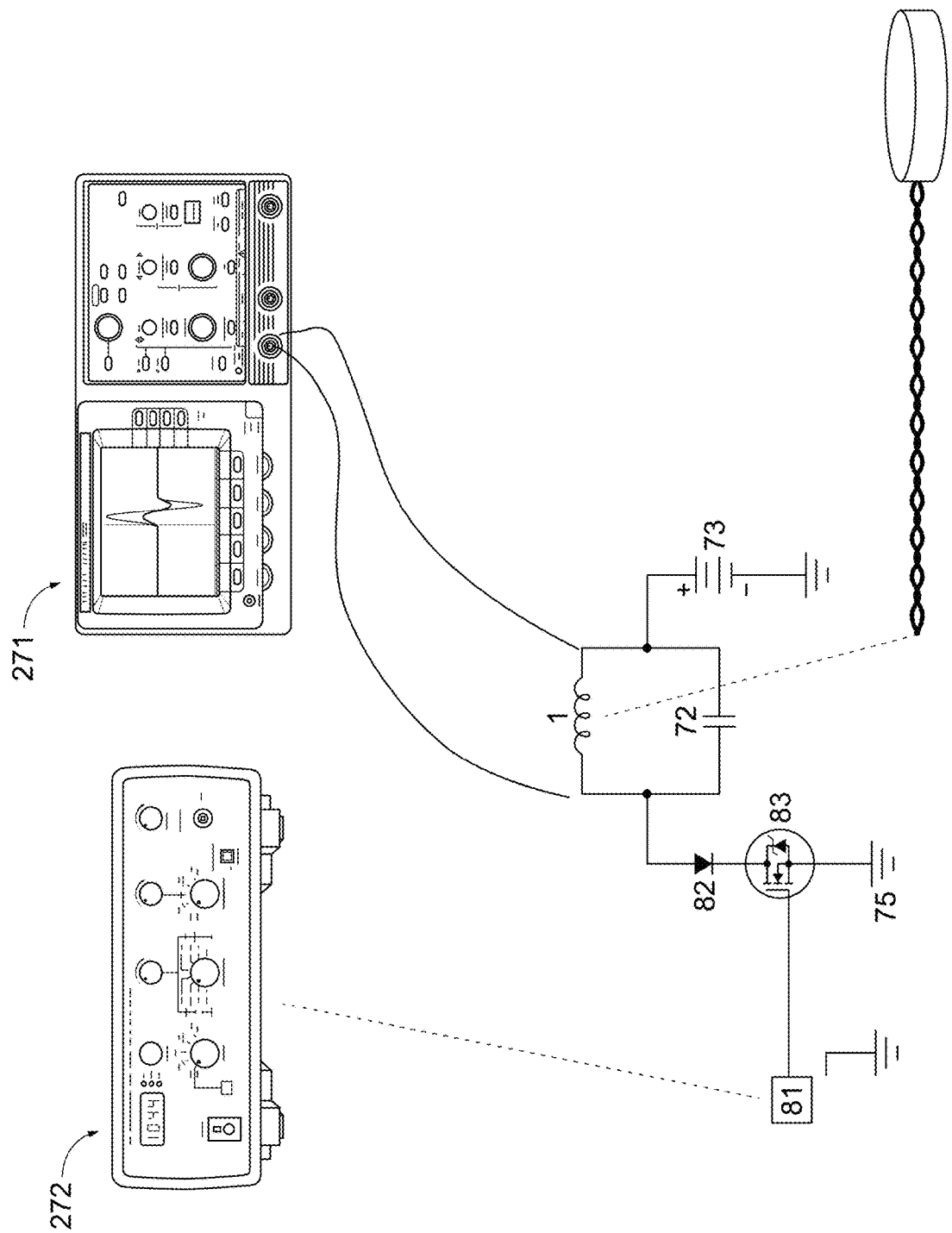
FIG. 27 shows the resonant pulse of the voltage in the stimulator coil during the experiment and the pulse generator displaying the stimulator's pulse rate.

FIG. 26 shows a higher magnification 100× of one endpoint of the injectable conductor 261. This endpoint is the target location for the stimulation to occur. An action potential sensor 262 was placed on another neuron cell about 200 microns away from the injectable endpoint 261. This sensor was used in the experiment to detect action potentials created by the Neural Stimulator's stimulation effect. FIG. 27 shows the stimulator coil voltage 271 on the oscilloscope, with a biphasic, charge-neutral, sinusoidal pulse shape. The repetition rate of burst is 104.4 Hz from the pulse generator 272 frequency. The amplitude of the coil 1 voltage was 1600 volts, and the period of the sinusoidal bi-phasic pulse was 130 microseconds. The power consumption of the stimulator coil and the driver circuit was 14 watts. In this demonstration, the stimulator coil was not turned off between stimulation bursts.

Figure 28:
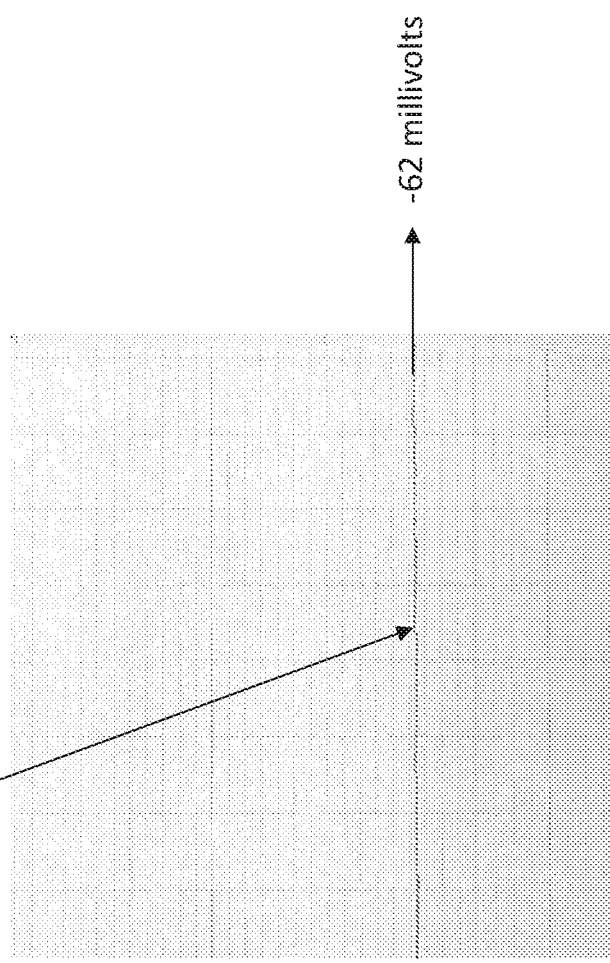
FIG. 28 shows the oscilloscope tracing of the resting potential of a sensed neuron when the stimulator is turned off.
Figure 29:
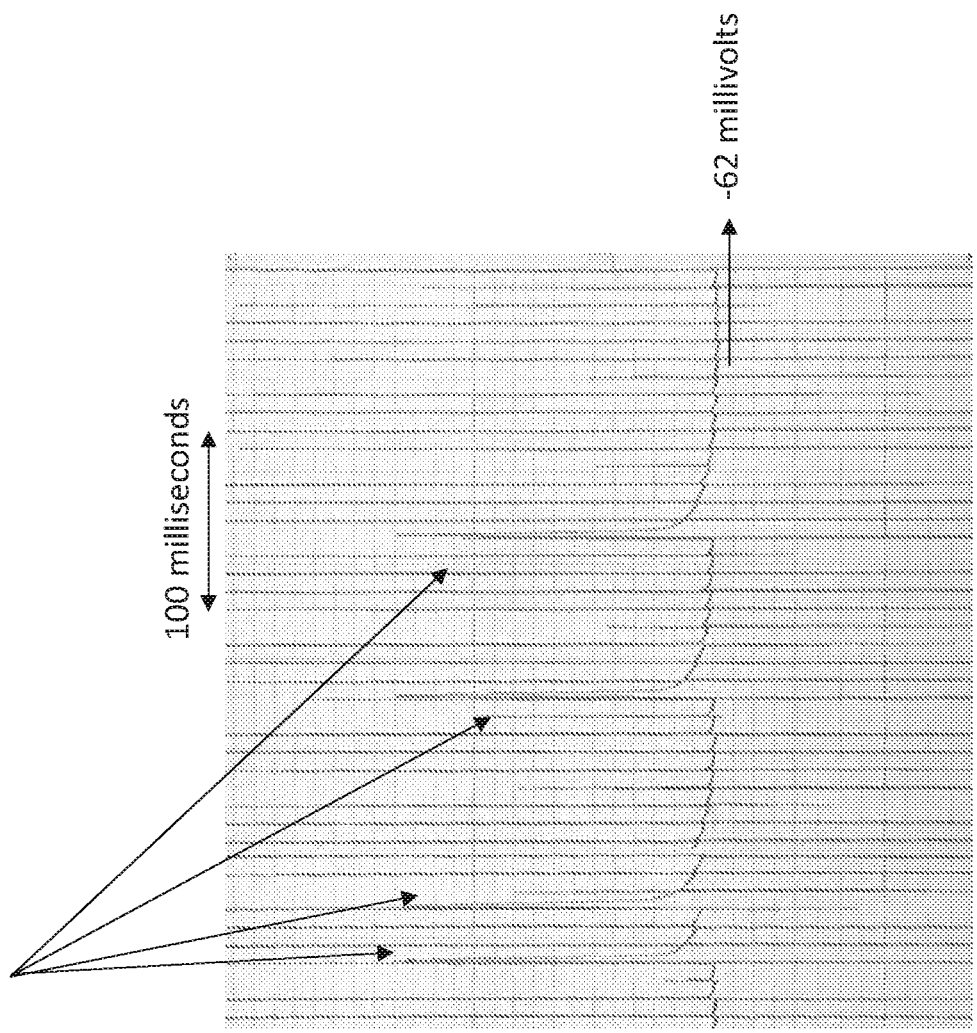

When the stimulator is not active, the sensor output is negative 62 millivolts, which is typical for a live mouse neuron resting potential 281 in FIG. 28. When the stimulator is turned on, a steady stream of stimulated action potentials 291 is evident in the nearby neuron by the output of the action potential sensor 262 in FIG. 26. The other, more frequent, pulses in the trace of FIG. 29 represent electromagnetic interference from the stimulator coil. Hence, the Neural Stimulator and its reduction to practice, as described, is effective in stimulating a targeted location in the brain, and this stimulation causes action potentials downstream in the neuronal network.

Wearable Housing

The wearable portion of this device contains at least the stimulator coil, which is facing the body and positioned as close as possible to the injectable conductor. The battery and driver circuit may be combined with the stimulator coil into one unit or these may be carried separately in a more convenient location. In most designs, the driver circuit fits into the center hole of the spool containing the windings of the simulator coil. This assembly is fully enclosed in a hard or partially flexible plastic housing. The thickness of the housing should be as thin as possible to minimize the distance from the coil windings to the injectable, but thick enough to be strong and uncompromised when dropped or after normal use or normal misuse. The housing must protect the user and others who handle it from the voltages generated inside. A contact sensor can turn the system off when not placed against the skin to save battery life and to prevent physical vibration of nearby ferromagnetic objects.

The coil and driver circuit assembly should be mounted snugly against the body using the aforementioned attachment methods, as the stimulation intensity will vary with the distance between the injectable and the coil windings. If the battery is not contained in this assembly, then wires are routed to the battery's location to bring power to the coil and driver circuit assembly.

Injection System and Method

FIG. 23 illustrates the injectable being placed by a syringe. The injectable conductor 3 passes through a syringe 231 with a hollow needle 234 to the appropriate position to be stimulated. First, the injectable conductor 3 is placed in the hollow needle 234 of the syringe 231, as illustrated in FIGS. 23a and 23b. Second, a longer cylinder 232 such as nylon thread, preferably non-conducting, of similar diameter pushes the injectable conductor through the needle until the injectable 3 is near the end of the needle. The placement of the conductor into the body is illustrated in FIGS. 23c to 23f. The needle 234 is inserted into the body 235, guided by an X-ray, fluoroscopy, CT, MRI, ultrasound, endoscopy or other real-time imaging system, until the tip of the needle is at the stimulation location 40. For example, B-mode ultrasound imaging may be employed with the imaging probe located to the left or right side of the body 235. Such a configuration would display an image of the cross-sectional plane that contains both the syringe needle and the ultimate placement of the injectable as well as a cross section of the nerve 40, enabling the surgeon or physician to place the injectable accurately. Then, a hand or mechanical gripper pushes the plunger 233 in FIG. 23a of the syringe 231, which pushes the injectable out of the needle. Once the injectable is pushed to the desired location near, the cylinder 232 in FIG. 23a is backed out by the gripper, and then the entire syringe 231 is backed out, leaving the injectable in place. In some embodiments where the injectable needs to be stimulated and the stimulation response observed to help guide the injectable to the target location, the wearable portion could be mounted nearby and activated during the injection. Without limitation, the needle could be preloaded with one or more injectable conductors and each one placed sequentially into nearby locations, and the injectable system be part of a kit and delivered in a sealed and sterile package.

Wearable Installation and Calibration

Once the injectable conductor is in the appropriate location, the wearable portion is mounted as it will be worn by the patient. The intensity of the stimulation is increased by slowly increasing the voltage to the driver circuit. When the desired amount of stimulation is achieved, that voltage level noted by the controller portion of the driver circuit. If appropriate, the attending physician will then specify a range of voltages around this level that the patient is able to set without supervision. If not appropriate, the patient will have a stimulation that was fixed by the physician, and cannot be changed without the physician present. If the patient does have ability to change the stimulation parameters, these can be accomplished through a smart phone or similar interface. Without limitation, the patient or attending physician could also have the liberty of adjusting the burst frequency, pulse shape, burst duration, pulse duration, and/or other parameter instead of or in addition to the voltage level. The desired amount of stimulation or other parameter could, depending on the nature of the treatment and the ability of the patient, be determined by feedback from patient or calibrated to a reference level based on feedback from other electrical signals in the body such as EKG, EMG, or other signal, or to another reference level pre-determined to be effective in a clinical trial. For example, EMG signals from healthy and connected muscles could be used to recruit and stimulate nerves connecting other muscles in the same muscle group that are unconnected due to pathology or injury. Another example is in prosthesis wherein the nerve is damaged, and the upstream nerve signals are used to trigger stimulation in the healthy downstream portion of the nerve. In the management of high blood pressure and heart rate the EKG or other signals could be used to trigger the stimulator to depolarize the neurons in the brain that create a sense of anxiety, thereby relaxing the entire neurological system.

Temporary and Permanent Installation

The methods just described can allow the patient to experience life with the Neural Stimulator active for a trial period, if desired. After the trial period, the patient and the attending physician will determine if the Neural Stimulator should be adjusted, terminated, or the injectable repositioned. Stimulation parameter adjustments can be made by re-using the feedback methods described for initial settings. If termination is desired, then the patient can likely continue a normal life with the injectable conductor in its current location, but not activate it with the wearable portion. The inactivated injectable conductor is not expected to cause complications in normal living or during MRI, X-ray, or other normal diagnostic procedure. If the injectable conductor is causing complications or the patient or physician wants it removed for another reason, then it can be removed using methods and tools that are used for a biopsy or removing cancerous tissue, such as keyhole surgery, guided by imaging such as functional MRI and/or ultrasound. If the injectable conductor needs to be repositioned, then another one could be placed downstream along the nerve pathway of the nerve to be stimulated, leaving the first injectable conductor in place. Or, the first injectable conductor may be removed and another one injected.

Figure 30:
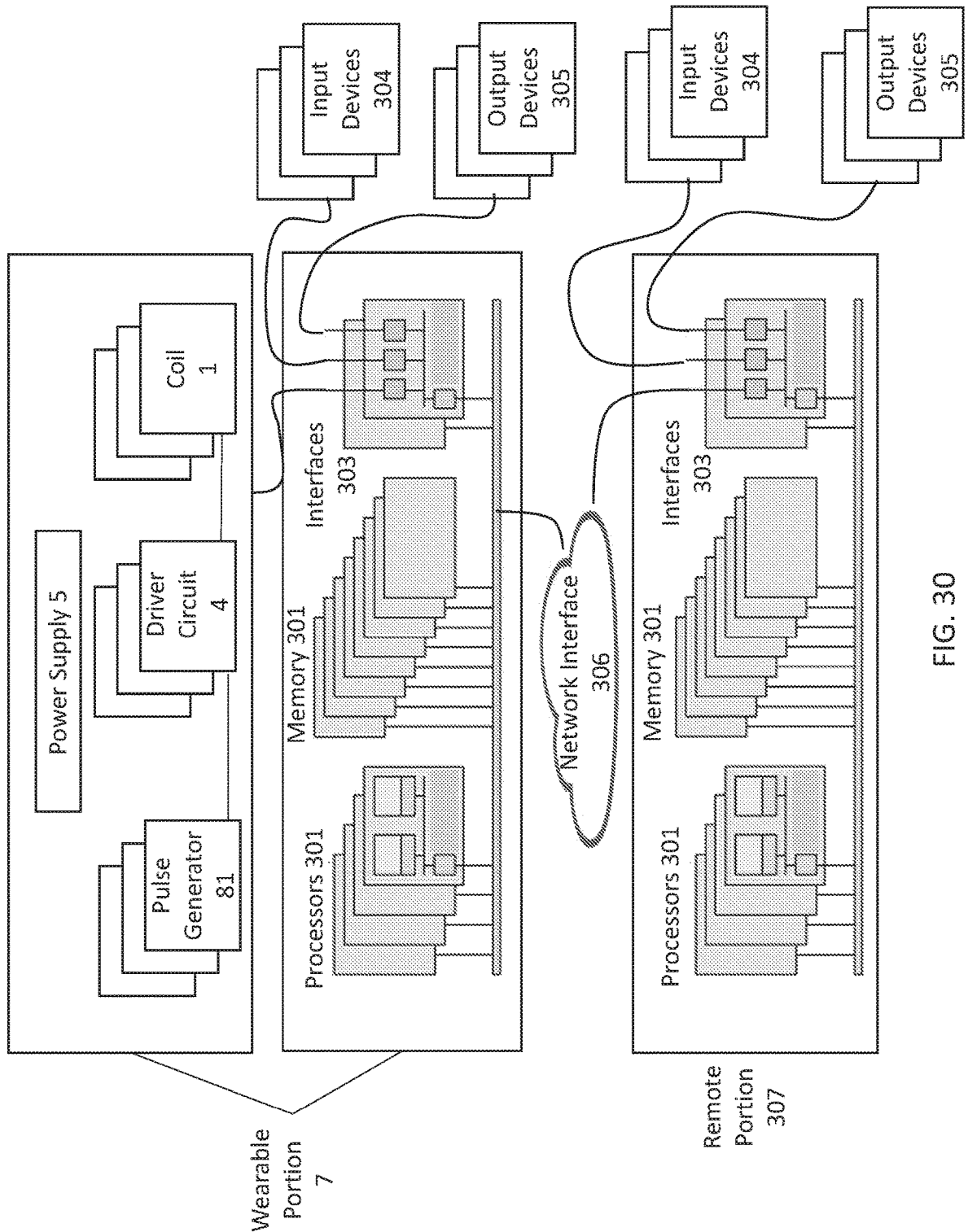
FIG. 30 depicts an exemplary system hardware architecture for the wearable system.

As noted previously, the driver circuit 4 in FIG. 1A may comprise a processing device, as schematically depicted in FIG. 30, which in turn may comprise a controller connected to one or more stimulation coils 1. The controller may comprise one or more processors 301 and one or more machine-readable memories 302 in communication with the one or more processors. The processor may incorporate data received from memory and operator input 304 to control the processing device. The inputs to the controller may be received from one or more machine generated and/or human generated sources (e.g., user input). The memory 302 may further store instructions to cause the processor 301 to execute modules, processes and/or functions associated with the processing device, such as the method steps described herein. The processor, memory, and interfaces may be local to the wearable device 7 or at a remote computing facility 307 in communication with the wearable 7 over a network interface 306.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers, or server computing devices such as routing/connectivity components, portable (e.g., hand-held) or laptop devices, multiprocessor systems, microprocessor-based systems, and distributed computing networks. Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like, and portable or wearable augmented reality devices that interface with an operator's environment through sensors and may use head-mounted displays for visualization, eye gaze tracking, and user input.

Processor

The processor may be any suitable processing device configured to run and/or execute a set of instructions or code and may include one or more data processors, image processors, graphics processing units, physics processing units, digital signal processors, and/or central processing units. The processor 301 in FIG. 30 may be, for example, a general-purpose processor, Field Programmable Gate Array (FPGA), an Application Specific Integrated Circuit (ASIC), and the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and the like.

Memory

In some variations, the memory 302 in FIG. 30 may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, and the like. As used herein, database refers to a data storage resource. The memory may store instructions to cause the processor to execute modules, processes and/or functions associated with the processing device (108), such as ECG signal data processing, communication, display, and/or user settings. In some variations, storage may be network-based as shown by 303 within the Remote Portion 307 in FIG. 30 and accessible for one or more authorized users. Network-based storage may be referred to as remote data storage or cloud data storage. Historical usage or physiological signal data stored in cloud data storage (e.g., database) may be accessible to respective users via a network, such as the Internet. In some variations, database may be a cloud-based FPGA.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for a specific purpose or purposes. Examples of non-transitory computer-readable media include, but are not limited to, magnetic storage media such as hard disks; optical storage media; holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, JAVA®, Python, Ruby, VISUAL BASIC®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

User Interface

A user interface may permit an operator to interact with and/or control the processing device directly and/or remotely. For example, the user interface may include an input device like 304 in FIG. 30 for an operator to input commands and an output device like 305 in FIG. 30 for an operator and/or other observers to receive output (e.g., view patient data on a display device) related to operation of the processing device.

User interface may serve as a communication interface between an operator and the processing device 301. In some variations, the user interface may comprise an input device 304 and output device 305 (e.g., touch screen and display) and be configured to receive input data and output data from one or more of the wearable portions 7, computing devices 301, input device 304, and output device 305. For example, physiological signal data generated by another device may be processed by processors 301 within wearable portion 7 or remote portion 307 and displayed by the output device 305 (e.g., monitor display). As another example, operator control of an input device 304 (e.g., joystick, keyboard, touch screen) may be received by user interface and then processed by controller 7 or 307 for user interface to output a control signal to one or more of the processing device 301.

Output Device

An output device 305 in FIG. 30 of a user interface may output historical or physiological signal data corresponding to a user, and may comprise one or more of a display device and audio device. The display device may be configured to display a graphical user interface (GUI). A display device 305 may permit an operator to view a physiological signal data and/or other data processed by the controller 7 or 307 or other device (not shown). In some variations, an output device 305 may comprise a display device including one or more of a light emitting diode (LED), liquid crystal display (LCD), electroluminescent display (ELD), plasma display panel (PDP), thin film transistor (TFT), organic light emitting diodes (OLED), electronic paper/e-ink display, laser display, and holographic display.

An audio device may audibly output subject data, sensor data, system data, alarms and/or warnings. In some variations, an audio device may comprise at least one of a speaker, piezoelectric audio device, magnetostrictive speaker, and/or digital speaker. In some variations, an operator may communicate with other users using the audio device and a communication channel. For example, the operator may form an audio communication channel (e.g., VoIP call) with a remote operator, technician, and/or subject.

Input Device

Some variations of an input device 304 in FIG. 30 may comprise at least one switch configured to generate a control signal. For example, an input device may comprise a touch surface for an operator to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, pointing device (e.g., mouse), trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio and recognize an operator voice as a control signal.

Network Interface

As depicted in FIG. 30, a processing device described herein may communicate with one or more networks and computing devices through a network interface 306. In some variations, the processing device may be in communication with other devices via one or more wired and/or wireless networks. For example, the network interface 306 may permit the processing device 301 in wearable portion 7 to communicate with one or more of a network 306 (e.g., Internet), remote server, and database. The network interface 306 may facilitate communication with other devices over one or more external ports (e.g., Universal Serial Bus (USB), multi-pin connector) configured to couple directly to other devices or indirectly over a network (e.g., the Internet, wireless LAN).

In some variations, the network interface 306 may comprise radiofrequency (RF) circuitry (e.g., RF transceiver) including one or more of a receiver, transmitter, and/or optical (e.g., infrared) receiver and transmitter configured to communicate with one or more devices and/or networks. RF circuitry may receive and transmit RF signals (e.g., electromagnetic signals). The RF circuitry converts electrical signals to/from electromagnetic signals and communicates with communications networks and other communications devices via the electromagnetic signals. The RF circuitry may include one or more of an antenna system, an RF transceiver, one or more amplifiers, a tuner, one or more oscillators, a digital signal processor, a CODEC chipset, a subscriber identity module (SIM) card, memory, and the like. A wireless network may refer to any type of digital network that is not connected by cables of any kind. Examples of wireless communication in a wireless network include, but are not limited to cellular, radio, satellite, and microwave communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet Message Access Protocol (IMAP) and/or Post Office Protocol (POP)), instant messaging (e.g., eXtensible Messaging and Presence Protocol (XMPP), Session Initiation Protocol for Instant Messaging and Presence Leveraging Extensions (SIMPLE), and/or Instant Messaging and Presence Service (IMPS)), and/or Short Message Service (SMS), or any other suitable communication protocol. Some wireless network deployments combine networks from multiple cellular networks or use a mix of cellular, Wi-Fi, and satellite communication. In some variations, a wireless network may connect to a wired network in order to interface with the Internet, other carrier voice and data networks, business networks, and personal networks. A wired network is typically carried over copper twisted pair, coaxial cable, and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). As used herein, network refers to any combination of wireless, wired, public, and private data networks that are typically interconnected through the Internet, to provide a unified networking and information access system.

Software Architecture

Figure 31A:
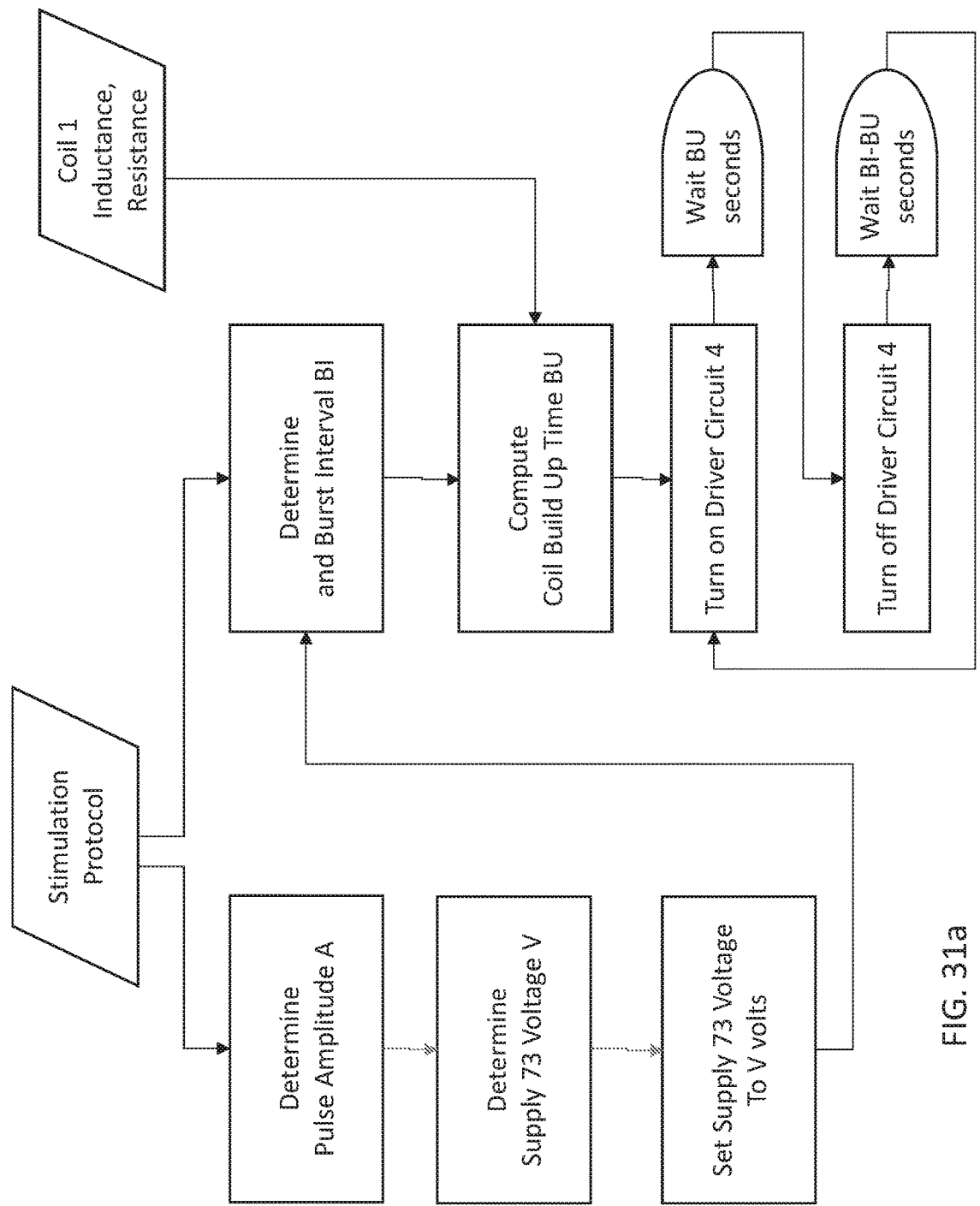
FIGS. 31a and 31b depict an exemplary software architecture for the wearable system, comprising a power saving mode and a pulse shape flexibility mode, respectively.
Figure 31B:
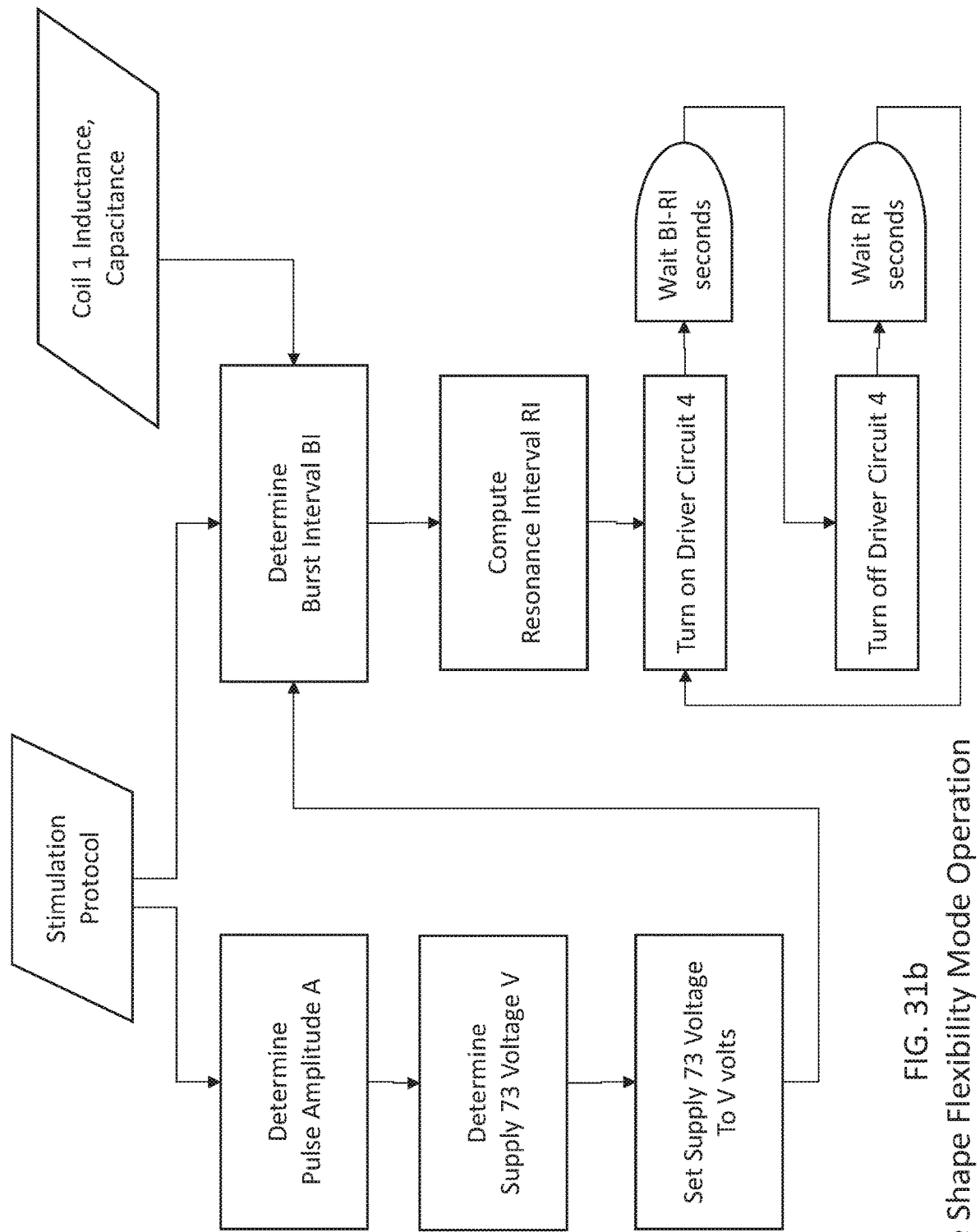

FIGS. 31a and 31b show the software architecture of the wearable portion of this Neural Stimulator. Two modes of operation are shown. FIG. 31a shows the mode of operation wherein power is saved by turning the system off in between bursts, which generates the fully and naturally decaying resonance bursts shown in FIG. 18b. FIG. 31b shows a mode of operation wherein the resonance is terminated after a number of resonant cycles, which could include fractional cycles, which generates the pulse shapes shown in FIGS. 15, 16, 18a, 19 and 20.

In FIG. 31a, the stimulation protocol determines the two parameters of the stimulator that are not hardware dependent in the embodiments shown thus far, and these parameters are the pulse amplitude and the burst interval, which designates the elapsed time between bursts of stimulation pulses. The pulse amplitude designated by the stimulation protocol sets the power supply 73 voltage, which is assumed to be programmable. The relationship between the supply voltage and the pulse amplitude generated at the injectable site is pre-determined during calibration of the system prior to injection in a simulated environment. This relationship is stored as a lookup table in the Memory 302 of the Wearable Portion 7 in FIG. 30. The stimulation protocol also designates the Burst Interval BI, which sets the periodicity of the switching of the Driver Circuit 4. In the power saving mode of operation, all power to the coil is turned in between bursts of pulses. Because of the inductance of the stimulator coil, the driver circuit must be turned on sufficiently prior to the burst to allow needed current to build up in the coil. The time needed for this buildup (BU) is related to the time constant L/R, wherein L is the inductance of the coil and R is the resistance of the coil plus any other resistances in the path from the power supply to ground. As illustrated in FIG. 31a, the coil is turned on for enough time for current to build up, which is the build-up time BU, Then, the stimulator is turned off, allowing the stimulator coil 1 and the parallel capacitor to resonate, generating a decaying series of bi-phasic sinusoidal pulses as illustrated in FIG. 18. The stimulator stays off until it is time to start building up the current in the coil again prior to the next burst, which is BI minus BU seconds.

FIG. 31b illustrates a different mode of operation, which consumes more power than the operation in FIG. 31a, but allows for more flexibility in pulse shapes, including the mono-phasic pulse shape illustrated in FIG. 20. The pulse amplitude is determined and set the same as was described for FIG. 30a. In this mode, the stimulator coil is normally turned on with full current flowing, even in between bursts. The steady current between bursts maintains a zero voltage at the injectable because the induced voltage, by Faraday's law, is the time derivative of the magnetic field, which is proportional to the coil current. When a burst is needed, the stimulator coil is turned off and is allowed it to resonate with the parallel capacitor for RI seconds, as the stimulation protocol designates. The stimulator in this case generates single or multiple periods of biphasic sinusoidal pulses or fractions thereof, as illustrated in FIG. 15, 16, 18a, 19 or 20. Once the resonance is stopped by the turning the stimulator coil back on after RI seconds, the controller waits until the next burst is required, which is the burst interval BI minus the resonance interval RI.

Although the present disclosure has been described in relation to various exemplary embodiments, various additional embodiments and alterations to the described embodiments are contemplated within the scope of the disclosure. Thus, no part of the foregoing description should be interpreted to limit the scope of the invention as set forth in the following claims. For all of the embodiments described above, the steps of the methods need not be performed sequentially.

I claim:

1. A neuromodulation system, comprising:
an external free running resonance magnetic field generator, comprising:
a housing;
a coil;
a capacitor connected in parallel with the coil such that a stimulation signal is a portion in time of a resonance between the parallel capacitor and coil;
a DC power supply at a first side of the parallel capacitor and coil, and configured to activate the parallel coil and capacitor; and
a switch to ground on a second side of the parallel capacitor and coil, wherein the switch comprises a microprocessor, a transistor and a rectifier;
wherein the microprocessor is configured to turn off a gate or a base of the transistor just prior to a first series of decaying resonant pulses to provide a free running resonance between the coil and the capacitor and then turn on the gate or the base to build up a current in the magnetic field generator prior to a second series of decaying resonant pulses to reduce electrical energy in the coil between the first and second series.

2. The neuromodulation system of claim 1, wherein the magnetic field generator further comprises an adhesive to attach the housing to a location on a human body.

3. The neuromodulation system of claim 1, further comprising a means for attaching the housing to a location on a human body.

4. The neuromodulation system of claim 1, wherein the magnetic field generator further comprises a battery.

5. The neuromodulation system claim 4, wherein the magnetic field generator further comprises a contact sensor, and wherein the magnetic field generator is configured to turn off and save battery life when not placed against skin.

6. The neuromodulation system of claim 4, wherein the battery is a rechargeable battery.

7. The neuromodulation system of claim 1, wherein the coil is a flexible coil.

8. The neuromodulation system of claim 7, wherein the flexible coil comprises a flexible circuit board.

9. The neuromodulation system of claim 7, wherein the flexible coil comprises a flexible material selected from a group consisting of BoPET, polyethylene, polyurethane, nylon and PTFE.

10. The neuromodulation system of claim 7, wherein the flexible coil comprises a flexible material with a thickness between 1 mm and 2 mm.

11. The neuromodulation system of claim 1, wherein the coil is a rigid coil.

12. The neuromodulation system of claim 11, wherein the coil has a thickness between 0.5 mm and 2.00 mm.

13. The neuromodulation system of claim 1, wherein the coil comprises an oval cross-section, with a long side of the oval cross-section configured to face a human body.

\* \* \* \* \*